US009681981B2

(12) United States Patent
Stevens

(10) Patent No.: US 9,681,981 B2
(45) Date of Patent: Jun. 20, 2017

(54) INTRAOCULAR IMPLANT AND METHOD FOR FIXING SAME INTO AN EYE

(71) Applicant: Julian Douglas Stevens, London (GB)

(72) Inventor: Julian Douglas Stevens, London (GB)

( * ) Notice: Subject to any disclaimer, the term of this patent is extended or adjusted under 35 U.S.C. 154(b) by 27 days.

(21) Appl. No.: 13/647,196

(22) Filed: Oct. 8, 2012

(65) Prior Publication Data

US 2013/0331937 A1 Dec. 12, 2013

Related U.S. Application Data

(63) Continuation-in-part of application No. 13/492,662, filed on Jun. 8, 2012.

(51) Int. Cl.
*A61F 2/16* (2006.01)
*A61F 9/00* (2006.01)
*A61F 2/14* (2006.01)

(52) U.S. Cl.
CPC ............. *A61F 9/0017* (2013.01); *A61F 2/14* (2013.01); *A61F 2/16* (2013.01); *A61F 2002/169* (2015.04); *A61F 2002/16902* (2015.04)

(58) Field of Classification Search
CPC ........ A61F 2/14; A61F 2/16; A61F 202/1608; A61F 2/1681; A61F 2/1697
USPC ....................... 623/5.15, 6.3, 6.43
See application file for complete search history.

(56) References Cited

U.S. PATENT DOCUMENTS

| 4,206,518 A | 6/1980 | Jardon |
| 4,262,370 A | 4/1981 | Hartstein |
| 4,485,498 A | 12/1984 | Gimbel |
| 4,642,114 A | 2/1987 | Rosa |
| 5,697,973 A | 12/1997 | Peyman |
| 6,051,024 A | 4/2000 | Cumming |
| 6,537,316 B1 | 3/2003 | Chambers |
| 2005/0256570 A1* | 11/2005 | Azar ............................ 623/5.14 |
| 2005/0288697 A1 | 12/2005 | Tei |
| 2006/0058812 A1 | 3/2006 | Terwee |
| 2006/0069433 A1* | 3/2006 | Nun ............................ 623/6.45 |

(Continued)

FOREIGN PATENT DOCUMENTS

WO WO 2007/082342 A1 7/2007

OTHER PUBLICATIONS

European Application No. 10251497.3-2320, European Search Report dated Feb. 2, 2011, 8 pages.

*Primary Examiner* — Christopher D Prone
*Assistant Examiner* — Christine Nelson
(74) *Attorney, Agent, or Firm* — Patterson Thuente Pedersen, P.A.

(57) ABSTRACT

An intraocular implant for use in a surgical procedure such as a cataract operation, or in a refractive-lens exchange surgery procedure, has a main portion and a peripheral portion peripheral to the main portion. The main portion is plate-like in shape and may be a lens or a plug for closing an aperture in the capsule of the eye. The implant has two or more lugs extending from the peripheral portion in a direction substantially perpendicular to a plane of the main portion. The lugs extend either from haptics, which protrude from the main portion, or from a short extension of the edge of the main portion. A method for fixing the implant into the eye involves making two or more voids in the capsule wall, offering up the implant to the capsule, so that the lugs lie adjacent to the voids, and inserting the lugs into the voids.

9 Claims, 24 Drawing Sheets

(56) References Cited

U.S. PATENT DOCUMENTS

| | | |
|---|---|---|
| 2006/0142856 A1 | 6/2006 | Willis |
| 2007/0088433 A1 | 4/2007 | Esch |
| 2008/0269883 A1 | 10/2008 | Das |
| 2010/0036488 A1 | 2/2010 | De Juan |
| 2010/0152847 A1* | 6/2010 | Padrick et al. .............. 623/6.11 |
| 2012/0078363 A1* | 3/2012 | Lu ............................... 623/6.37 |

* cited by examiner

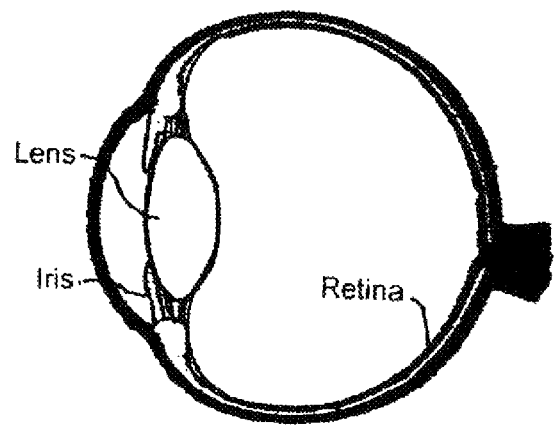
Fig. 1
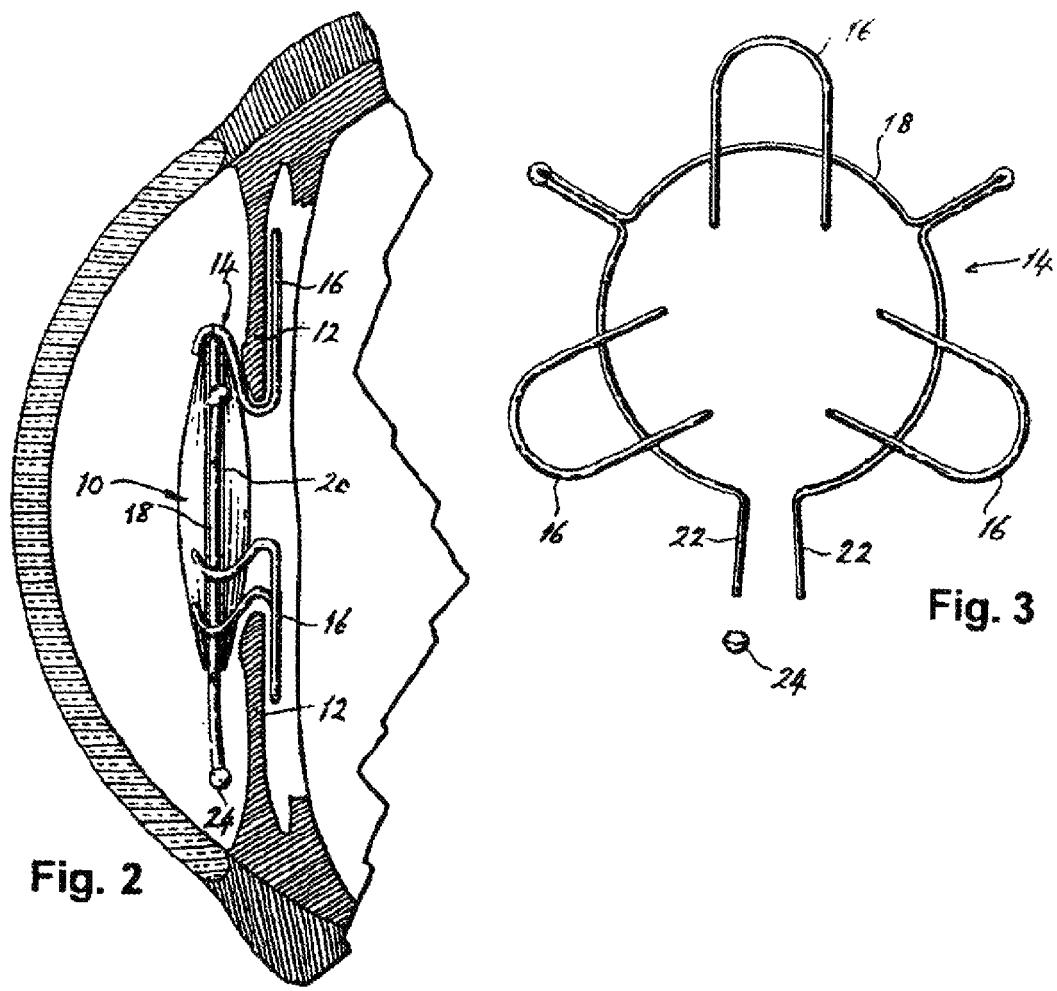
Fig. 2
Fig. 3

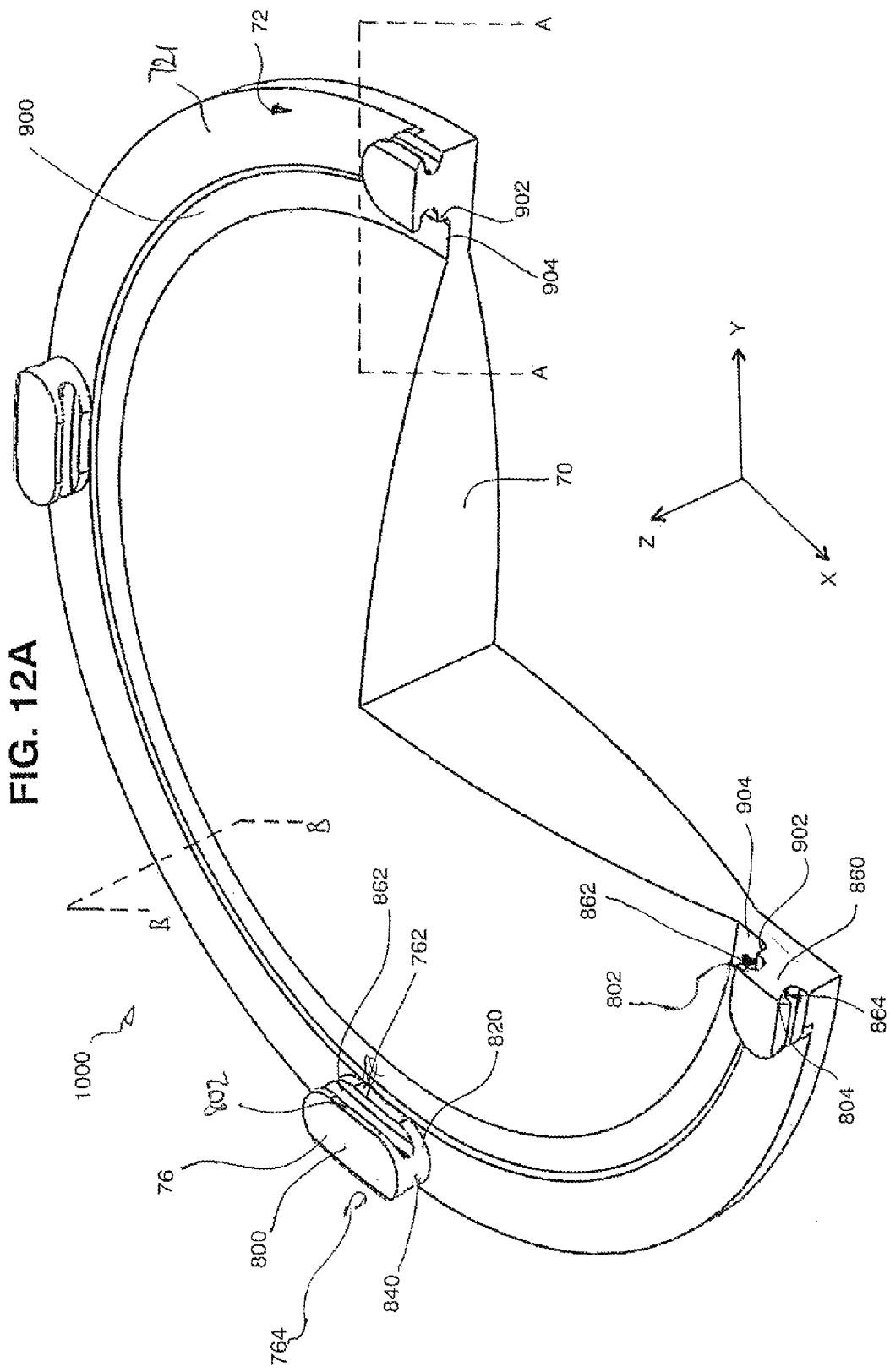

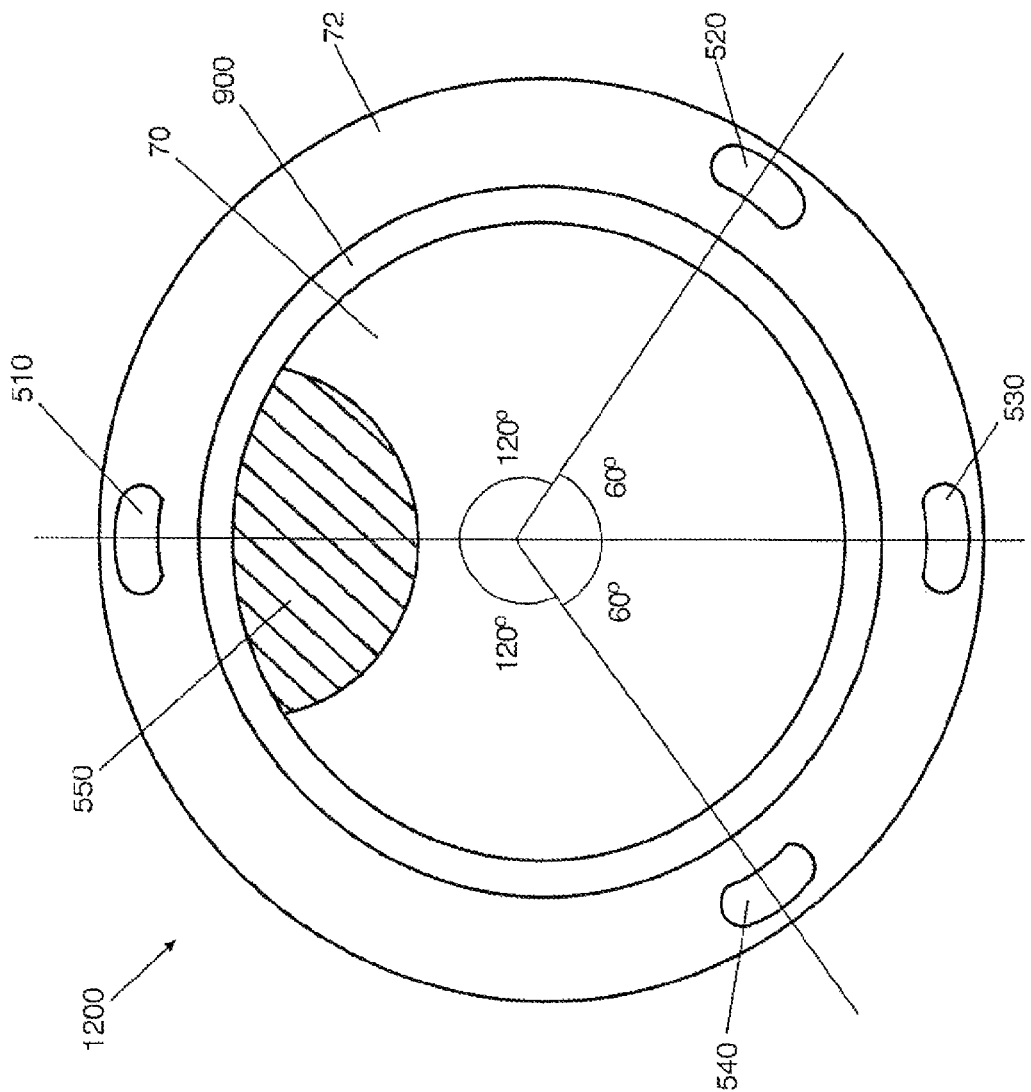
FIG. 15
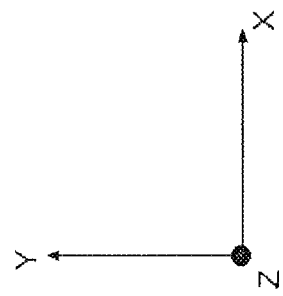

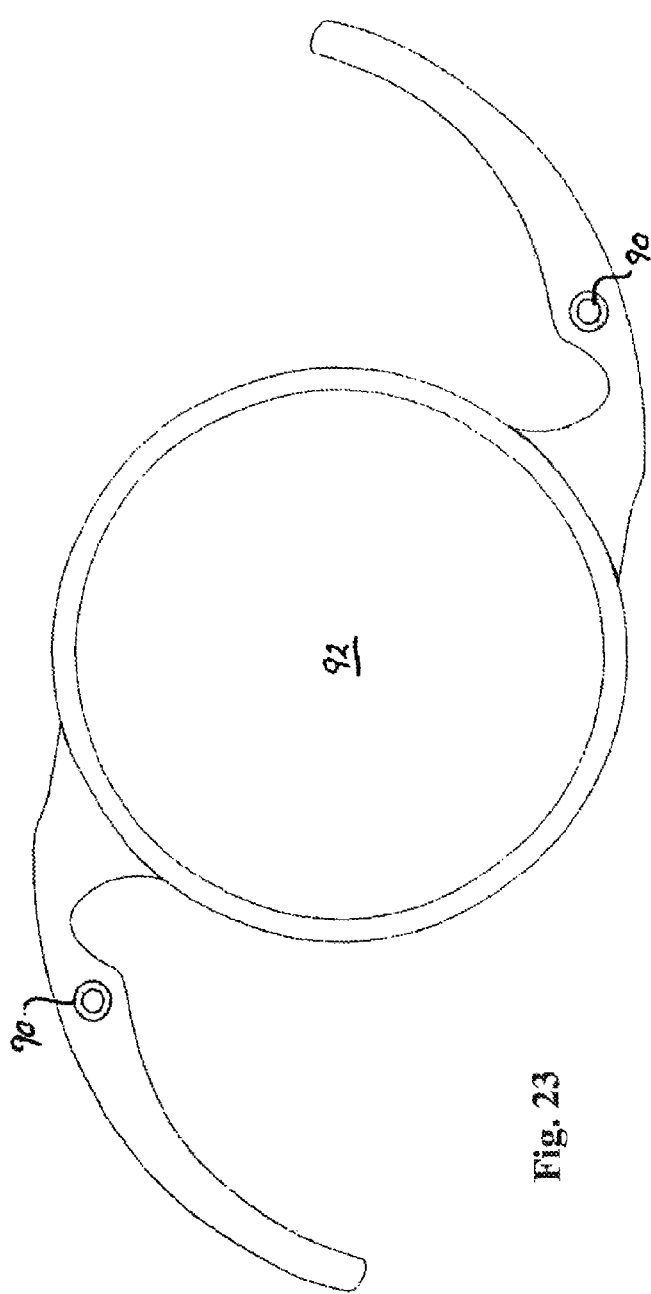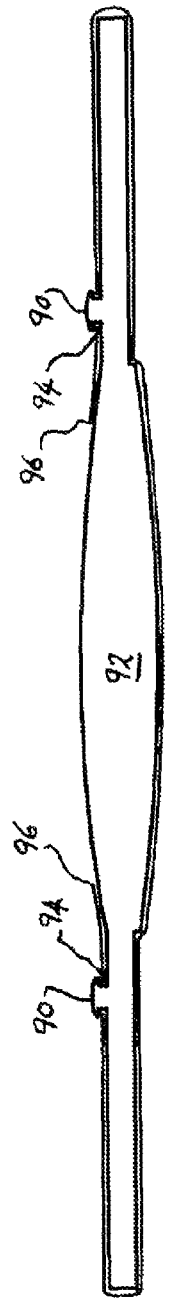

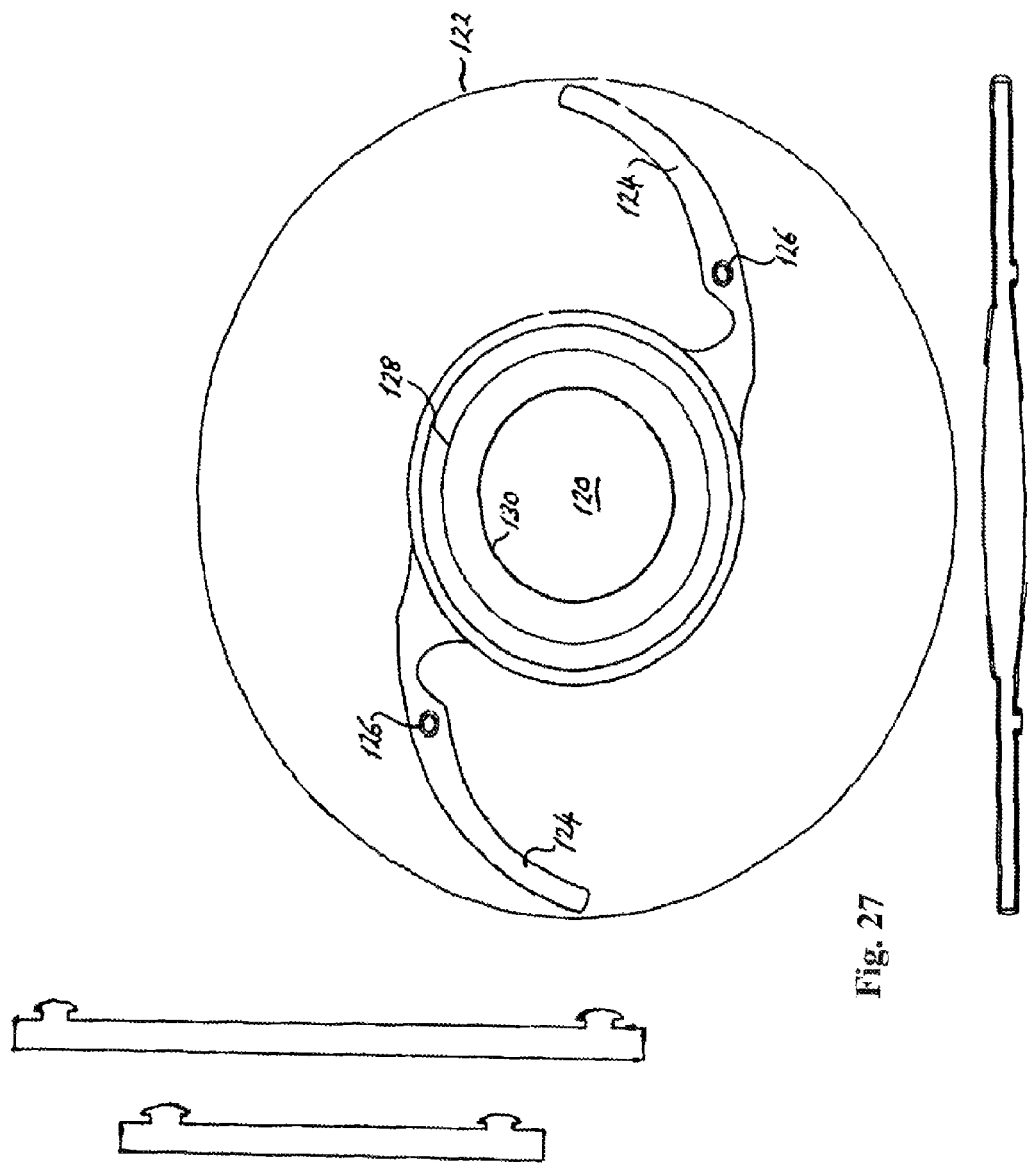

INTRAOCULAR IMPLANT AND METHOD FOR FIXING SAME INTO AN EYE

CLAIM TO PRIORITY

This application is a continuation-in-part of U.S. application Ser. No. 13/492,662 entitled "Intraocular Implant and Method for Fixing Same Into an Eye" filed on Jun. 8, 2012, the entire contents of which are incorporated herein by reference.

FIELD OF THE INVENTION

The invention relates to intraocular implants in general, and to intraocular implants for use in cataract operations or refractive crystalline lens extraction operations. The invention also relates to a method for fixing such intraocular implants into an eye.

BACKGROUND OF THE INVENTION

The cataract condition is a well known eye ailment, which these days is easily treatable through surgery. The condition involves an opacification of the lens (see FIG. 1), which is situated just behind the iris and serves to focus the incoming image onto the retina at the back of the eye. The surgical procedure involves the removal of the opaque lens and its substitution by an artificial lens having the required focusing effect.

One way of achieving this is described in U.S. Pat. No. 3,925,825. FIGS. 2 and 3 correspond to FIGS. 1 and 2 of this patent, and show the placing of a lens 10 anterior to the iris 12. The lens is held in place against the iris by a haptic section 14. The haptic section 14 consists of a series of bent wire loops 16, which are attached to a circular wire frame 18. The lens 10 has a flat circumferential face 20 and the lens is held within the frame 18 by inserting the lens inside the frame 18 and closing the legs 22 of the frame so that the frame 18 closes tightly against the lens face 20. Once the legs 22 have been brought together, their ends are kept together via a terminal part 24.

One way of extracting the opaque natural lens—a process known as extra-capsular extraction—will now be described. Reference is first made to US 2003/0130732, FIG. 1 of which corresponds to FIG. 4 of the present application. The lens 30 is accommodated within a so-called capsule (also sometimes referred to as a "capsular bag", or simply "bag"), which is shown as item 32 in FIG. 4. To remove the opaque lens, an opening (a so-called "capsulotomy") is made in the anterior part 34 of the capsule 32 manually by a surgeon or by a pulsed laser and the lens 30 is removed through the opening.

To facilitate the removal of the opaque lens, the lens is first emulsified by the phacoemulsification method or by a pulsed laser. Phacoemsulification involves making a small incision in the cornea and introducing a very thin needle through the incision, which is then brought into contact with the lens through the capsulotomy. The needle is caused to vibrate at an ultrasonic frequency by the use of a magnetostrictive driver. The ultrasonic vibrations of the needle soften the lens and emulsify it. The emulsified parts can then be aspirated out of the capsule through the incision. Finally, the incision is widened sufficiently to introduce the substitute artificial lens into the capsule. A pulsed laser can be used to create an opening in the capsule, by photoablating capsular tissue along a predetermined boundary, which can be circular or elliptical if desired.

Like the lens of FIG. 2, the lens in the extra-capsular method is conventionally held within the capsule by the use of haptics. One example of this is shown in U.S. Pat. No. 5,376,115. FIGS. 5 and 6 are an extract from this patent, in which the artificial lens 36 with its haptics 38 is introduced through the iris and into the capsule 40 via the capsulotomy (FIGS. 5) and finally brought to bear against the inside posterior surface of the capsule (FIGS. 6). The haptics 38 are used to center the lens and secure it in place inside the capsule.

SUMMARY OF THE INVENTION

One problem associated with the known capsular insert technique is that it is difficult to center the lens accurately in the X-Y plane (coronal plane) of the eye. (The X-Y-Z co-ordinates are shown in FIGS. 7 and 8.) This is the case, even though the haptics are supposed to center the lens as close to the optical axis of the eye as possible. The reason for this is that the pupil of the eye, which is the opening of the iris, is not necessarily centered with respect to the capsule. Hence the lens can be centered with respect to the capsule, but not with respect to the pupil.

It is also difficult to ensure that the lens has the desired placement in the rotational direction in the X-Y plane. A third problem is that, due to the presence of the haptics, the known technique requires a fairly large incision in the eye in order to be able to introduce the implant into the eye, whereas it is always desirable to be able to minimize the degree of intervention, including the size of the incision.

A further drawback is the difficulty of accurately defining the location of the lens in the Z-direction. This can lead to difficulties in defining the required optical power of the lens.

It is an aim of the intraocular implant according to the present invention to mitigate these drawbacks associated with the known implant techniques.

The present invention provides an intraocular implant for placement in the eye. According to a first aspect of the invention, there is provided an intraocular implant for placement in the eye, the implant comprising a main portion and a peripheral portion peripheral to the main portion, the implant having at least two lugs extending from the peripheral portion in a direction substantially perpendicular to a plane of the implant, the lugs being for engagement with corresponding voids provided in a capsule of the eye, and at least one of the lugs extending further in a circumferential direction of the main portion than in a radial direction.

In an example embodiment, the at least one lug has a race track shape in plan view. The race track shape may comprise rounded ends joined by straight sides. According to another example embodiment, the race track shape is at least one of an ellipse and an ovoid.

According to another example embodiment, the at least one lug comprises a top and a bottom joined by a stem.

According to another example embodiment, a groove is disposed to run along the length of each a radially inward side and a radially outward side of the at least one lug, the groove being disposed between the top and the bottom. According to an example embodiment a radially inward groove is distinct from a radially outward groove.

According to another aspect of the invention, the peripheral portion comprises a short extension of the main portion over the entire periphery of the main portion, the extension of the main portion comprising the at least two lugs.

The lugs may be substantially equidistantly spaced around the peripheral portion.

According to another example embodiment, the at least two lugs each comprise a neck portion, which extends from the peripheral portion in the direction substantially perpendicular to the plane of the lamina, and a head portion extending from the neck portion.

According to an aspect of the invention, the lugs have a rounded top.

Where a groove is provided, it may have a width, in the direction substantially perpendicular to the plane of the implant, approximately equal to the thickness of a wall of the capsule. For example, the groove has a width in a range 30 to 50 micrometres.

According to another embodiment, the implant is a lens, the main portion of the implant comprising the optic of the lens.

According to another aspect of the invention, there is provided an intraocular implant for placement in the eye, the implant comprising a main portion and a peripheral portion peripheral to the main portion, the implant having at least two lugs extending from the peripheral portion in a direction substantially perpendicular to a plane of the implant, the lugs being for engagement with corresponding voids provided in a capsule of the eye, at least one of the lugs extending further in a circumferential direction of the main portion than in a radial direction, and when viewed in plan view, the at least one lug comprising rounded ends joined by one concave side and one convex side.

For example, the convex side is radially outward of the concave side.

According to another aspect of the invention, there is provided an intraocular implant for placement in the eye, the implant comprising a main portion and a peripheral portion peripheral to the main portion, the implant having at least two lugs extending from the peripheral portion in a direction substantially perpendicular to a plane of the implant, the lugs being for engagement with corresponding voids provided in a capsule of the eye, the implant further comprising a groove between the at least two lugs and the main portion.

According to an example embodiment, the groove comprises a riser disposed on its radially outward side and according to another example embodiment the groove comprises a bottom between the riser and the main portion. According to an example embodiment, the main portion forms a further radially inward riser of the groove.

According to an example embodiment, the width of the groove is between 0.1 mm and 0.5 mm in a radial direction of the implant.

According to a further aspect of the invention, there is provided a lug for attachment to a peripheral portion of an intraocular implant for placement in the eye, the implant comprising a main portion and the peripheral portion peripheral to the main portion, the lug being for engagement with a corresponding void provided in a capsule of the eye. In example embodiments, the shape of the lug is as described above.

The present invention also provides a method of manufacturing an intraocular implant for placement in the eye, the method comprising providing an implant body comprising a main portion and a peripheral portion peripheral to the main portion; providing a plurality of lugs; and attaching the plurality of lugs to the peripheral portion.

In an example embodiment, an outer contour of the lug has the same shape as part of an outer edge of the peripheral portion, the method comprising aligning the outer contour of the lug with the outer edge of the peripheral portion.

The lugs may be attached, for example, by laser welding or adhesive.

Recesses may be formed in the peripheral portion, and the plurality of lugs may be fitted in respective recesses.

In another aspect of the invention, there is provided an intraocular implant for placement in the eye, the implant comprising a main portion and a peripheral portion peripheral to the main portion, the implant having at least two lugs extending from the peripheral portion in a direction out of a plane of the implant, the lugs being for engagement with corresponding voids provided in a capsule of the eye, and the lugs being asymmetrically arranged.

The lugs may be asymmetrically arranged by being located at positions asymmetric about at least one direction in the plane of the implant. Alternatively, the lugs are asymmetrically arranged by at least one said lug having a different shape to another said lug.

For example, a distance between a first said lug and a second said lug, which is adjacent to the first said lug, is different than a distance between the first said lug and a third said lug, which is adjacent to the first said lug on the opposite side to the second said lug.

According to an example embodiment, there are four lugs; the first lug is located 120° from the fourth lug, which is adjacent to the first lug; the first lug is located 60° from the second lug, which is adjacent to the first lug on the opposite side to the fourth lug; the third lug is located 120° from the fourth lug, which is adjacent to the third lug; and the third lug is located 60° from the second lug, which is adjacent to the third lug on the opposite side to the fourth lug.

According to an example embodiment, the main portion is a lens having variable optical power and for example the main portion is a toric lens. The lens may be formed based on a measurement of a patient's eye, and that at least one lug is aligned with a landmark of the eye the lens is to correct. According to an example embodiment, the landmark is a principal meridian of at least one of anterior and posterior corneal curvature astigmatism or a canthus.

According to another example embodiment, at least one lug is located at a predetermined position with respect to a patient's eye, irrespective of the prescription of the eye the lens is to correct.

In another aspect of the invention, there is provided an intraocular implant for placement in the eye, the implant comprising a main portion and a peripheral portion peripheral to the main portion, the main portion being asymmetrical, the implant having at least two lugs extending from the peripheral portion in a direction out of a plane of the implant, the lugs being for engagement with corresponding voids provided in a capsule of the eye, and the lugs being located with respect to the main portion such that, when the voids are provided in the capsule at a same predetermined landmark, the implant can be implanted by engaging the voids to achieve correct rotational registration of the main portion with respect to the eye.

According to an example embodiment, the main portion is a toric lens or at least the main portion is a lens having variable optical power.

According to another example embodiment, the lugs are asymmetrically arranged with respect to the main portion, and for example the lugs are asymmetrically arranged by means of being asymmetrically located.

In a further aspect of the invention, there is provided a method of eye surgery on a patient, comprising fitting an intraocular implant, the implant comprising a lens and a peripheral portion peripheral to the lens, the implant having at least two lugs extending from the peripheral portion in a direction out of a plane of the implant, the lugs being for engagement with corresponding voids provided in a capsule of the eye, the lugs being asymmetrically arranged and the lens having variable optical power to correct vision of the patient, the method comprising: measuring the eye to determine the location of a meridian; performing a capsulotomy including forming the corresponding voids in the capsule of the eye, at least one of said voids being aligned with the meridian; and engaging the at least two lugs in the corresponding voids, whereby the lens is rotationally aligned to correct the patient's vision.

For example, the meridian is a principal meridian of at least one of anterior and posterior corneal curvature astigmatism.

According to another example embodiment, the method further comprises earlier steps of: measuring the patient's eye to determine its shape; and making the implant based on the determined shape to correct the patient's vision.

BRIEF DESCRIPTION OF THE DRAWINGS

Embodiments of the present invention will now be described, by way of example only, with reference to the drawings, in which:

FIG. 1 is a sectional view of the human eye;

FIG. 2 is a part-side and part-sectional view of a human eye with an artificial lens substituted for the original lens in accordance with a known method;

FIG. 3 shows a haptic arrangement used in the known method of FIG. 2;

FIG. 12A is a partial sectional view of an intraocular implant according to a third example embodiment of the present invention;

FIG. 15 is a top view of an intraocular implant according to a fifth example embodiment of the present invention;

FIGS. 21-28 are various examples of lenses in place in a bag;

FIG. 29 depicts two examples of a plug-type implant according to an eleventh example embodiment of the present invention;

DETAILED DESCRIPTION OF THE EMBODIMENTS

Figure 4:
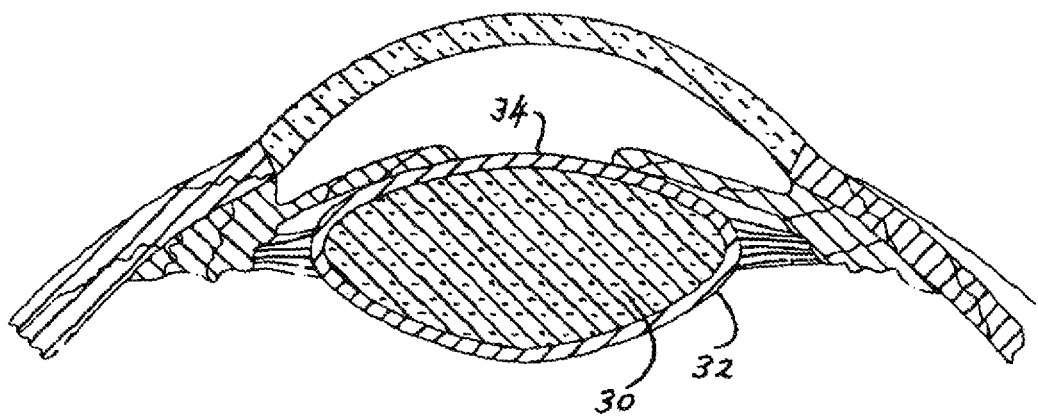
FIG. 4 is a sectional view of a human eye showing the natural lens in its capsule.
Figure 5:
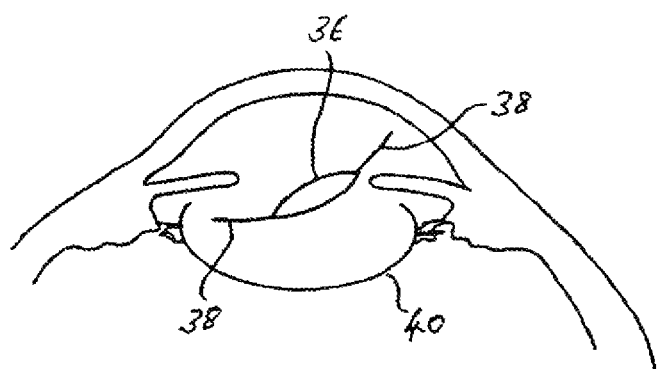
FIGS. 5 and 6 are sectional views showing two stages in a known lens replacement method employing extra-capsular extraction.
Figure 6:
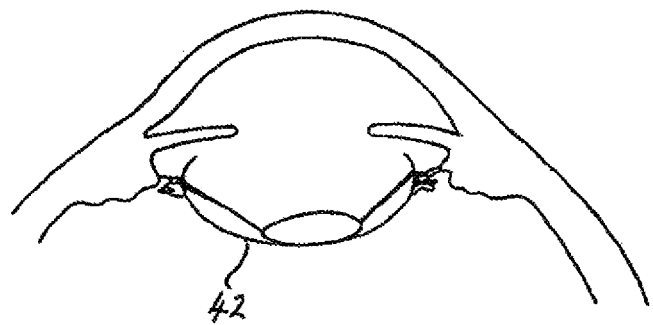
Figure 7:
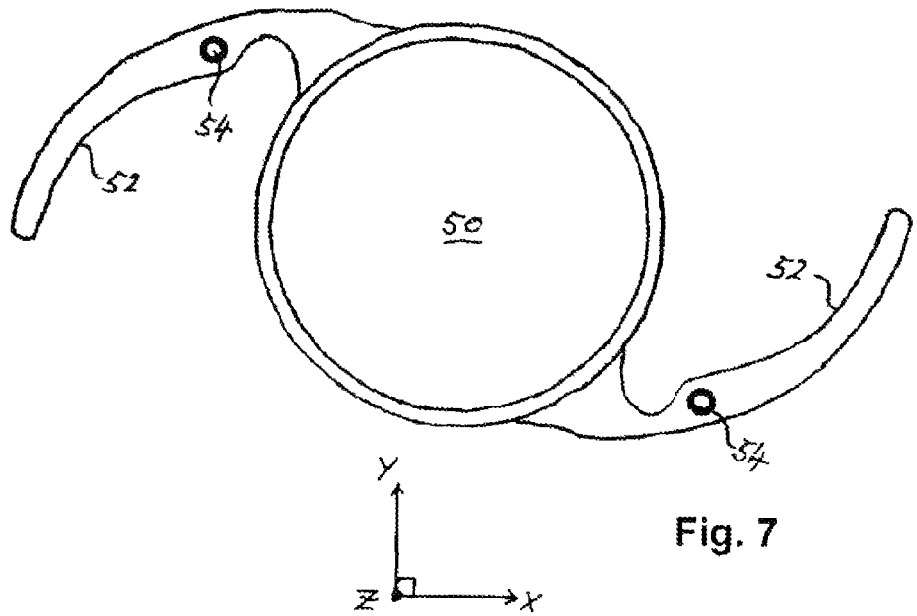
FIGS. 7 and 8 are front and top views, respectively, of an intraocular implant in accordance with a first example embodiment of the invention.
Figure 8:
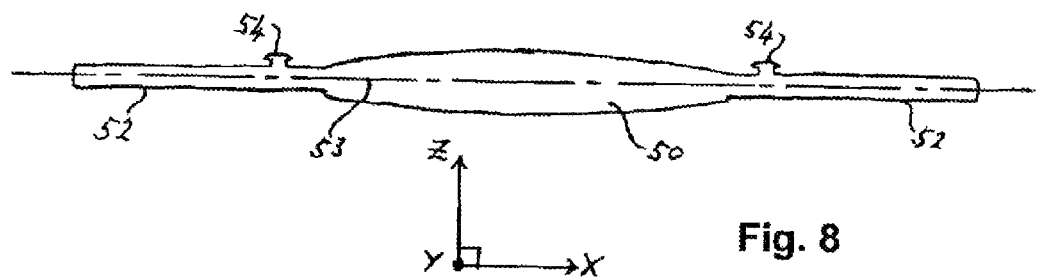
Figure 9:
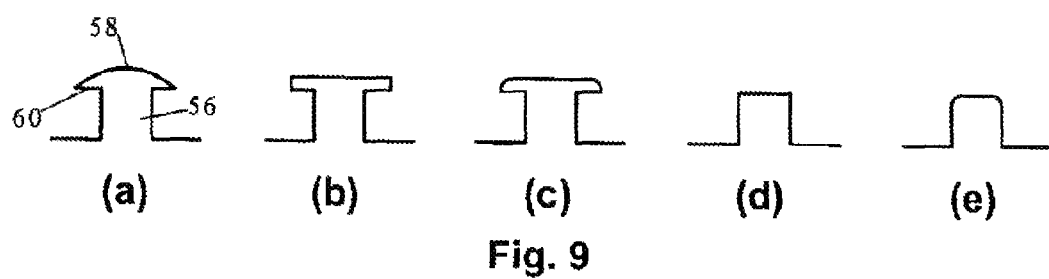
FIGS. 9(a)-9(e) are enlarged views of different versions of the lug shown in FIGS. 7 and 8.

FIGS. 7 and 8 depict an intraocular lens comprising the lens proper (the "optic") 50 and a pair of haptics 52. The optic is a lamina, i.e. roughly plate-shaped, so that its diameter (assuming a circular profile) is much greater than its thickness, especially at the edges. Extending from each haptic at a point part-way along its length is a lug 54. The lugs are configured in this example as shown in, e.g., FIG. 9(a) and have a neck 56 and a head 58 and are of one piece with the respective haptics. The lugs extend in a direction substantially perpendicular to the plane 53 of the lamina. In one example of its use, the lens is inserted into the capsule of the eye through a capsulotomy previous made in the eye and is secured to the capsule by inserting each lug through a void or incision made in the capsule by suitable means. In this respect convenient use can be made of the modern femtosecond pulsed laser technique, which enables voids of very accurate size and location to be made in the capsule by laser-pulse photoablation along a predetermined boundary. This means that the lens can be produced as a standard item with the lugs 54 disposed at a standard distance apart from each other and from the optical center of the optic, leaving it up to the surgeon to form voids of the correct location and size in the capsule to suit this standard distance.

The head 58 of the lugs in this embodiment is, but need not be, mushroom-shaped (see FIG. 9(a)), which facilitates the insertion of the lug into the void made in the capsule. By contrast the surface 60 of the head behind the mushroom surface is desirably linear, to discourage the lug from coming out of the void of its own accord. Thus, the void will normally be a through-hole of a diameter approximately equal to that of the neck of the lug. In addition, the neck of the lug will normally be of a length approximately the same as, but can be somewhat greater than the anticipated thickness of the capsule wall (which is approximately 20 micrometres). A typical range of values for the length of the neck is 30 to 50 micrometres and for the diameter of the neck is 100 to 500 micrometres.

The profile of the lugs may be other than mushroom-shaped, provided it allows relatively easy insertion of the lugs into the voids in the capsule wall. Thus, the lug may have a "T"-shaped cross-section, as shown in FIG. 9(b). A variant of this "T" profile is FIG. 9(c), in which the outer edge is chamfered, making it easier to insert. Also, while the inclusion of a head is to be preferred, for the reason given in the preceding paragraph, it is not absolutely essential. Thus, the invention also envisages the use of a lug as shown in FIG. 9(d) or FIG. 9(e). In FIG. 9(d) the lug consists of just the neck, which has a square top. A variant of this, similar to that shown in FIG. 9(c), is a rounded-top version illustrated in FIG. 9(e). Where the lug is headless, it may be expedient to ensure a fairly tight fit between the lug and the capsule void, in order to discourage migration of the implant away from the capsule.

As regards the profile of the lugs in plan view (view orthogonal to the sectional view of FIG. 9), this is circular, though other profiles may also be suitable.

Figure 10:
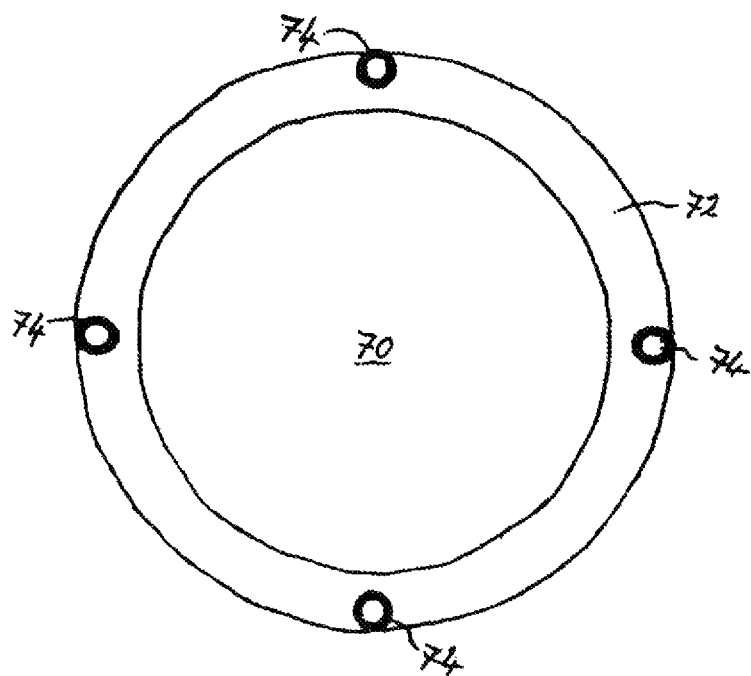
FIGS. 10 and 11 are front and top views, respectively, of an intraocular implant in accordance with a second example embodiment of the invention.
Figure 11:

A second example embodiment of the implant in accordance with the invention is illustrated in FIGS. 10 and 11.

Here the implant has no haptics, but consists of the optic 70 plus a peripheral section 72, which is a simple extension of the edge of the optic. The radial width of the extension will be at least sufficient to accommodate the lugs and to ensure that the voids made in the capsule are reasonably remote from the lip of the capsulotomy. Four lugs 74 protrude from, and are of one piece with, the peripheral section, being substantially equidistantly spaced around the peripheral section. The lugs 74 are configured as in the first example embodiment (see FIG. 9).

This implant is smaller than that of the first example embodiment, since no haptics are present. This means that the incision to be made in the eye, in order to introduce the implant into the eye, can be made smaller, with a smaller wound and leading to a faster recovery of the patient.

Figure 12B:
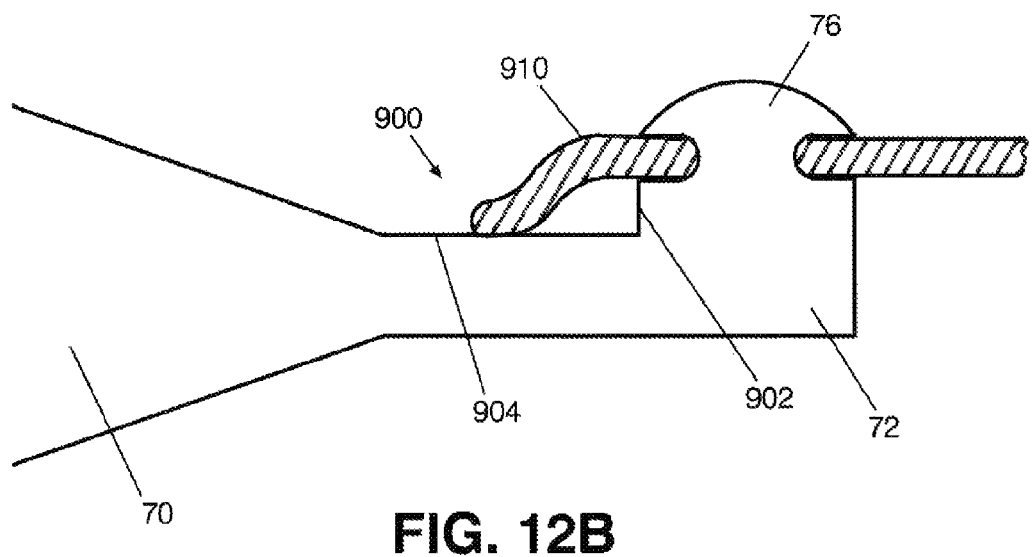
FIG. 12B is a sectional view of the portion A-A shown in FIG. 12A.
Figure 13:
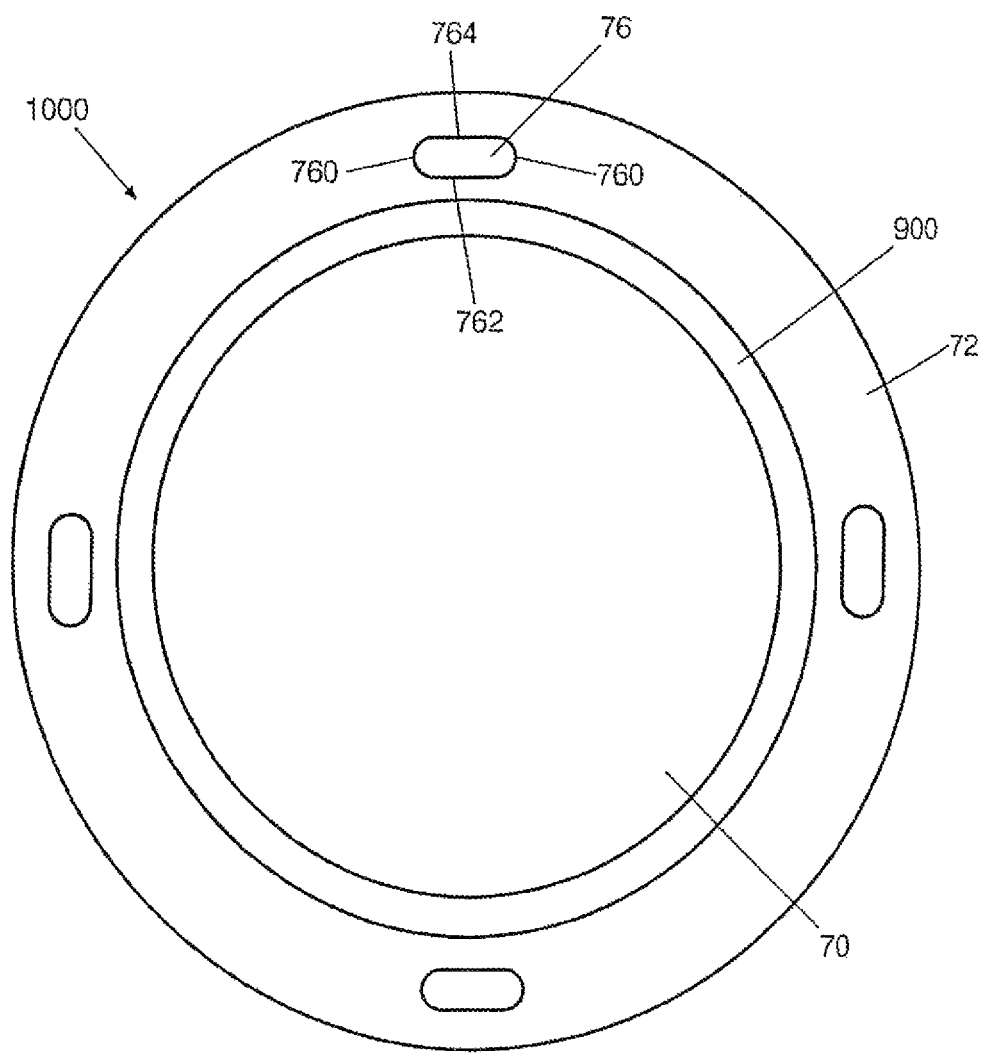
FIG. 13 is a top view of a variation of the intraocular implant of the third example embodiment of the present invention.

An implant 1000 according to a third embodiment of the invention is shown in FIGS. 12A & B and FIG. 13. The implant 1000 of the third example embodiment is similar to that of the second example embodiment and like features will be referred to using like reference numbers. Thus, as in the second embodiment, the implant 1000 of the third example embodiment comprises an optic 70 with a peripheral skirt 72 or section, which is a simple extension of the optic 70. Again, lugs 76 are mounted on the skirt 72. As in the other embodiments, the implant 1000 can be said to have a plane in the X and Y directions. However, the third example embodiment differs from the second example embodiment in a number of important respects and these will be discussed below.

In the third example embodiment, the lugs 76 are not circular in plan view, but rather have what may be termed a race track shape in which the "race track" is longer than it is wide and has rounded ends. According to one example, the race track shape comprises substantially two semicircles 760 joined by inner and outer straight edges 762, 764 (see FIG. 13). Alternatively, the race track shape may be an elliptical or ovoid shape.

As can be seen in FIG. 12A, each lug comprises a race track-shaped top 800 and a similarly race track-shaped bottom 820 joined by a stem 860. The bottom 820 is integral with the skirt 72 so that the lug 76 is provided in a fixed location with respect to the optic 70.

Between the top 800 and the bottom 820 there are formed a radially inner groove 862 and a radially outer groove 864 running along the length of the radially inner and outer sides 762, 764 respectively. The inner and outer grooves 862, 864 sandwich the stem 860 between them. In the present example embodiment, the grooves 862, 864 are distinct from one another, although it is possible for a single groove to run around the entire periphery of the lug 76. By providing a separate groove 862, 864 on each side of the lug 76, the top 800 is provided with distinct inner and outer lips 802, 804 respectively. The height of the grooves in the Z direction may be substantially the same as or slightly greater than the thickness of the capsule wall 910 (see FIG. 12A). Thus, the height of the grooves is, for example, 30 to 50 µm. The depth of the grooves in the X-Y plane (coronal plane) extending away from the inner and outer edges 762, 762 respectively is, for example, also in the range 30 to 50 µm.

The top 800 of the lug 76 can have a curved upper surface—that is, the upper surface of the top 800 curves upwards out of the X-Y plane. This assists the surgeon in placing the lugs 76 in the voids (incisions) created in the capsule and minimises irritation to the iris. The overall height of the lugs 76 in the Z direction and the degree of curvature is also chosen to provide a low profile to avoid chafing the iris. The overall geometry of the lugs is likewise selected to avoid causing irritation to the patient.

Providing a lug 76 of this shape has several other advantages over the previously described lugs. First, because each lug 76 has a race track shape in plan view, it is elongated in the circumferential direction of the optic 70. This elongation provides two benefits. First, the provision of the long lips 802, 804 and the long grooves 862, 864 open at both ends 760 assists in more securely fitting the lugs 76 in the voids made in the capsule wall 910. In particular, portions of the capsule at the edges of the voids are able to fit snugly in and along the length of both the inner and outer grooves 862, 864 provided between the top 802 and bottom 804 of the lugs 76 to hold the optic 70 in place securely. The long inner and outer lips 802, 804 are disposed in situ on the opposite side of the capsule to the bottom 820 of the lug 76 to hold the implant in place.

In addition, providing the elongated, race track shape has the benefit that the stem 860 is also thicker in the circumferential direction of the optic 70. Given the diaphanous nature of the material from which the lug is made, this provides significant additional strength to the lug 76, ensuring the integrity of the top 800 of the lug 76 with the remaining portions in long term use in vivo. In particular, the lug 76 is more resistant to, and less likely to be damaged by, the patient rubbing his eyes or other physical shock and manipulation.

It will be noted that since the grooves 862, 864 are provided distinct from one another, the circumferential sides 840 of the lug 76 are substantially flat in the Z direction. Thus, the stem 860 extends for the full length of the lug 76 in substantially the circumferential direction of the optic 70. This further increases the strength of the lug 76.

Moreover, by providing the lug in this shape, the length of the incision made in the capsule can exactly or substantially match the length of the elongated lug 76. Thus, the ends of the incision made in the capsule wall 910 do not need to be stretched in the circumferential direction of the implant 1000 to fit over the head before falling into a narrower groove. This allows for a tight fit between the ends 840 of the lug 76 and edge of the incision made in the capsule wall 910, thereby assisting in more securely engaging the lug 76 in the void with better accuracy in rotational engagement.

Since the lug 76 is elongated in the circumferential direction of the optic 70, it is not necessary to extend the radial width of the peripheral skirt 72 to achieve the above-mentioned benefits.

Figure 12C:
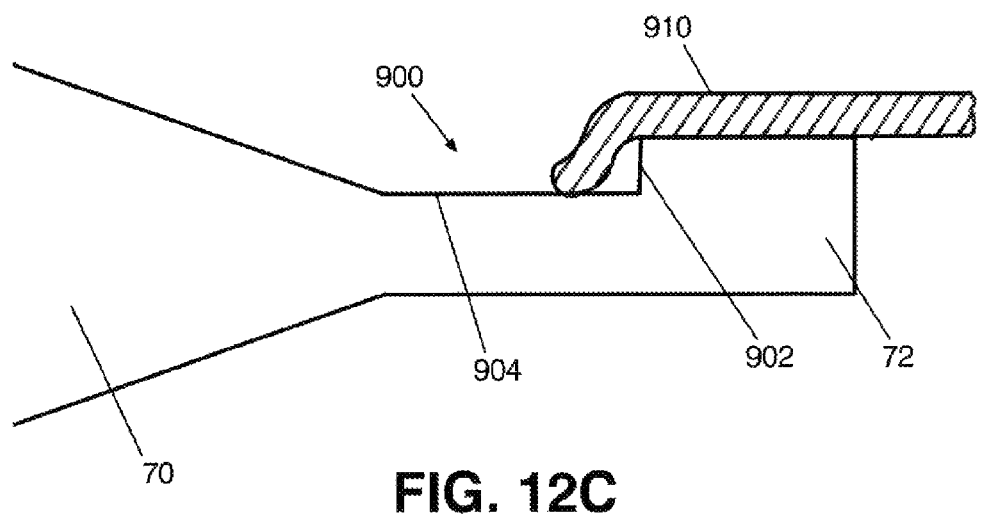
FIG. 12C is a sectional view of the portion B-B shown in FIG. 12A.

According to one embodiment of the invention, the width of the lug 76 in the radial direction of the implant 1000 is substantially the same as the width of the peripheral skirt 72, as shown in FIG. 12. Thus, the overall diameter of the implant can be minimised. However, this is not an essential requirement. Thus, FIG. 13 shows a variation of the embodiment shown in FIG. 12, in which the width of the lug 76 in the radial direction is smaller than that of the peripheral skirt 72. In FIG. 13 the lugs are provided substantially in the middle of the peripheral skirt in the width direction. However, they may be provided anywhere and are, for example, provided so that the outer edge of the lugs is adjacent or the same as the outer edge of the peripheral skirt.

In the event that it is found during surgery that it is not possible to properly form the voids/incisions into which the lugs 76 are to be fitted, the outer edge of the capsulotomy may be fitted to the outside grooves 864 of the implant 1000. Because the lugs 76 are elongated in the circumferential direction of the optic 70, this reduces amount of the capsule wall overlying the optic 70 or eliminates it completely. While such a situation is not ideal, in particular because rotational registration becomes difficult or is no longer possible and mounting of implant 1000 is less secure, it at least provides the surgeon with a back up procedure so that he can ensure that the patient's sight is restored.

The implant 1000 further comprises a circumferential groove 900 formed on the same surface of the skirt 72 as the lugs 76 and disposed between the optic 70 and the peripheral skirt 72, and hence each of the lugs 76. As shown in FIGS. 12A, B and C, the groove 900 comprises a radially outer side wall 902 and a bottom surface 904 extending radially inwards up to the optic 70. Thus, the side wall 902 creates a step between the outer part of the peripheral skirt 72 on which the lugs 76 are formed and the bottom surface 904 of the groove 900. According to an example embodiment, the optic 70 borders the bottom surface 904, but an inner side wall radially opposite to the outer side wall 902 may be provided between the bottom surface 904 and the optic 70. It will be appreciated that the optic 70 itself may be sufficiently thick that it creates such an inner side wall bordering the bottom surface 904.

The circumferential groove 900 allows the capsule to sit flush with the implant 1000 in vivo as shown in FIGS. 12B & C. In particular, the capsule wall 910 forming the edge 400 of the capsulotomy may drop over the side wall 902 into the groove 900, for example, to lie against the bottom surface 904 of the groove 900. This has the significant benefit of providing an effective barrier between the exterior of the capsule and its interior. In addition, the provision of the groove 900 is effective to prevent or reduce the formation or movement of epithelial cells under the edge of the capsulotomy.

FIG. 12B also shows the lug 76 engaged with the capsule by dint of being pushed through a void in the capsulotomy so that the edges of the incision lie within the grooves 862, 864 between the upper and lower lips 802, 804, 806, 808.

Figure 14A:
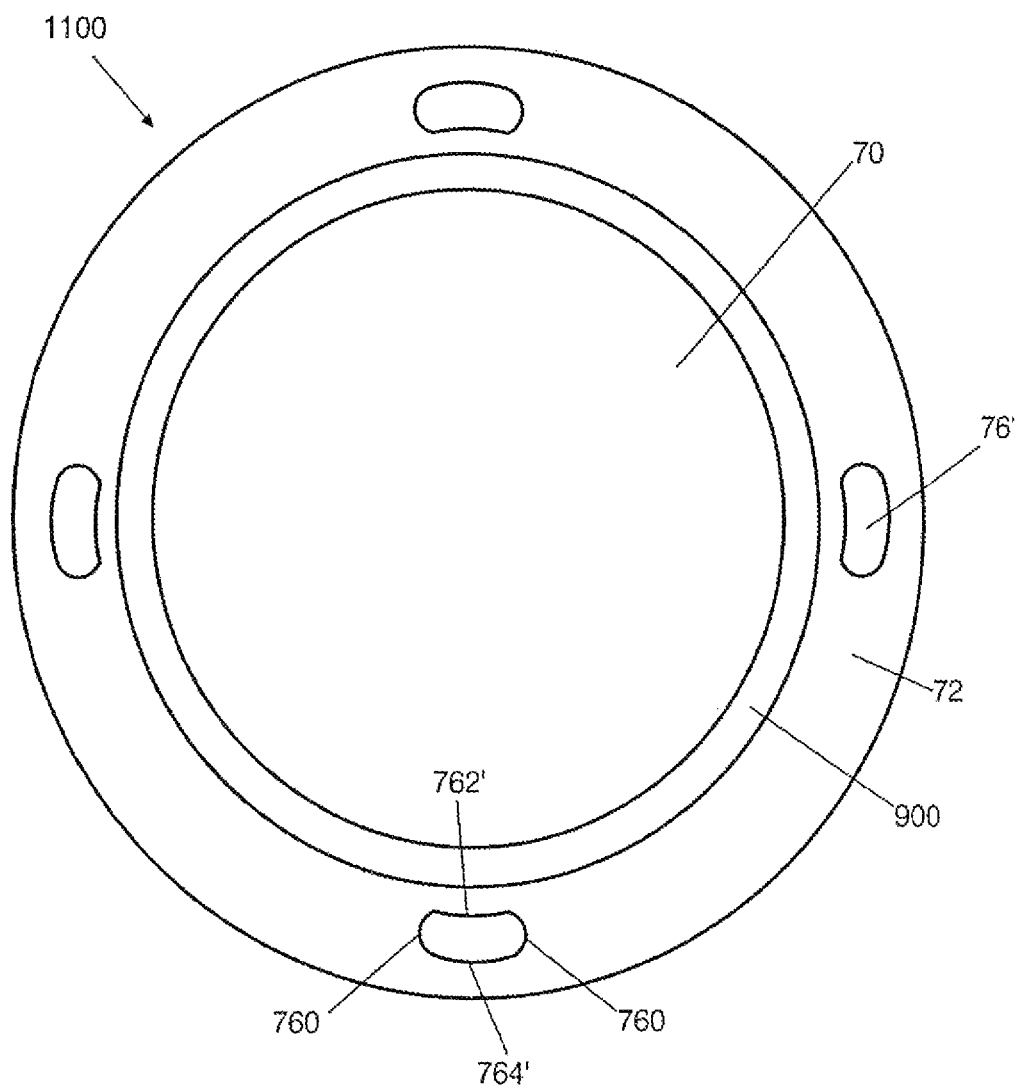
FIG. 14A is a top view of an intraocular implant according to a fourth example embodiment of the present invention.

FIG. 14A shows a plan view of an implant 1100 according to a fourth example embodiment of the present invention. The implant 1100 of the fourth example embodiment differs from that of the third example embodiment only in the shape of the lugs 76'. As shown in FIG. 14, in the implant 1100 the lugs 76' are what may be described as kidney-shaped. In particular, like the lugs 76 shown in FIG. 12 they include substantially two semicircles 760 at the sides in a circumferential of the implant joined by radially inner and outer edges 762', 764'. However, in this case the radially inner and outer edges 762', 764' are not straight but instead are curved. In more detail, the radially inner edge 762' is concave whereas the radially outer edge 764' is convex and parallel to the radially inner edge 762'.

Figure 14B:
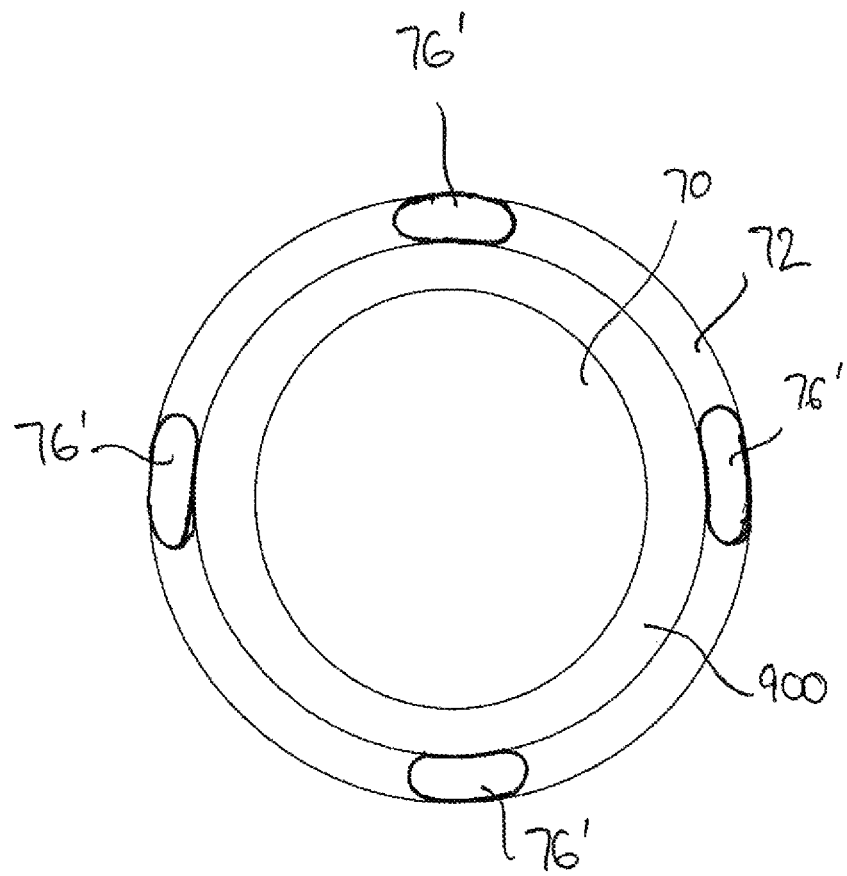
FIG. 14B is a top view of a variation of the intraocular implant of the fourth example embodiment of the present invention.

According to an example embodiment, as shown in FIG. 14B, the radially outer edge 764' follows the outer circumference of the peripheral skirt 72 and the radially inner edge 762' follows the inner circumference of the peripheral skirt 72.

The provision of a kidney-shaped lug 76' in this manner, with a concave radially inner edge 762' is advantageous compared with a straight edge in that it allows the lug 76' to be disposed closer to the optic 70 without falling within the patient's line of sight and with little or no scattering or reflection of light from the lug 76' to affect a patient's vision. Accordingly, the implant 1100 of this example embodiment provides an improved optical experience for the patient without compromising the security of the fitting of the lugs 76' in the incisions in the capsule and while maintaining the structural strength and integrity of the lugs 76' of the third example embodiment.

In the foregoing example embodiments, the lugs are disposed in a symmetrical arrangement around the optic 70. However, in other example embodiments the lugs are disposed in an asymmetrical arrangement. An implant 1200 according to a fifth example embodiment having such an asymmetrical arrangement is shown in FIG. 15.

As in the third and fourth example embodiments, the implant 1200 comprises an optic 70 having a peripheral skirt 72 with a circumferential groove 900 surrounding the optic 70. It also comprises four lugs 510-540. However, in this case the lugs are disposed asymmetrically. In particular, the first lug 510 is disposed at 12 o'clock, the second lug 520 at 4 o'clock, the third lug 530 at six o'clock and the fourth lug 540 at 8 o'clock. Thus, the first lug 510 is at 120° to the second and fourth lugs 520, 540, whereas the third lug 530 is at 60° to the second and fourth lugs 520, 540. Although the lugs 510-540 are symmetrically located with respect to the Y axis, they are asymmetrical with respect to the X axis. Moreover, they are asymmetrical about a line in the X-Y plane passing through the center of the optic and the center of at least one lug and so are termed asymmetrical for the purposes of this specification.

The shaded area 550 in FIG. 15 represents a part of the lens having a different optical power to the remaining part of the lens. The position of the part having the different optical power 550 relative to each of the lugs 510-540 is predetermined. In particular, the first lug 510 is positioned opposite the center of the part having the different optical power 550. In the same way, for any toric or otherwise asymmetrical optic, the first lug 550 can be positioned to show the rotational geometry or other variation.

Thus, when the surgeon comes to fit the implant, he is able to determine its rotational geometry from physical inspection of the implant 1200 and hence where the part having the different optical power 550 is. The orientation of the implant 1200 can be referenced to measureable landmarks of a patient's eye, such as the principal meridian of anterior or posterior corneal curvature astigmatism measureable by optical coherence tomography (OCT) scanning during the lens surgery procedure, so there can be rotational registration with respect to such landmarks. The surgeon can then make incisions in the capsule corresponding to the lugs 510-540 at the respective positions required to achieve the desired rotational registration.

In particular, since the position of the first lug 510 can be easily distinguished from that of the other lugs 520-540, the surgeon can make the incision for the first lug 510 at the required rotational position in the capsule so that the part having the different optical power 550 is correctly located with respect to the pupil. The incisions for the other lugs 520-540 can be made at corresponding positions.

The asymmetric positioning of the lugs 510-540 around the skirt 72 is particularly suitable where the optic 70 is itself asymmetrical, for example where the lens has variable optical power or there is a toric optic. The asymmetrical positioning of the lugs 510-540 is especially desirable for the treatment of astigmatism by a toric lens. In particular, this has the significant advantage of ensuring that the surgeon can easily locate the implant 1200 with the correct rotational registration.

It should also be appreciated that asymmetry can also be achieved by providing at least one of the lugs with a different shape to the other lugs, or by orienting at least one of the lugs differently to the other lugs.

It should be noted that the concept of providing the lugs 510-540 at a predetermined position with respect to the asymmetry of the optic 70 is separable from the concept of providing the lugs 510-540 themselves at asymmetrical positions. However, the synergistic combination of the two concepts allows for accurate rotational registration with a significantly reduced likelihood of error.

Figure 16:
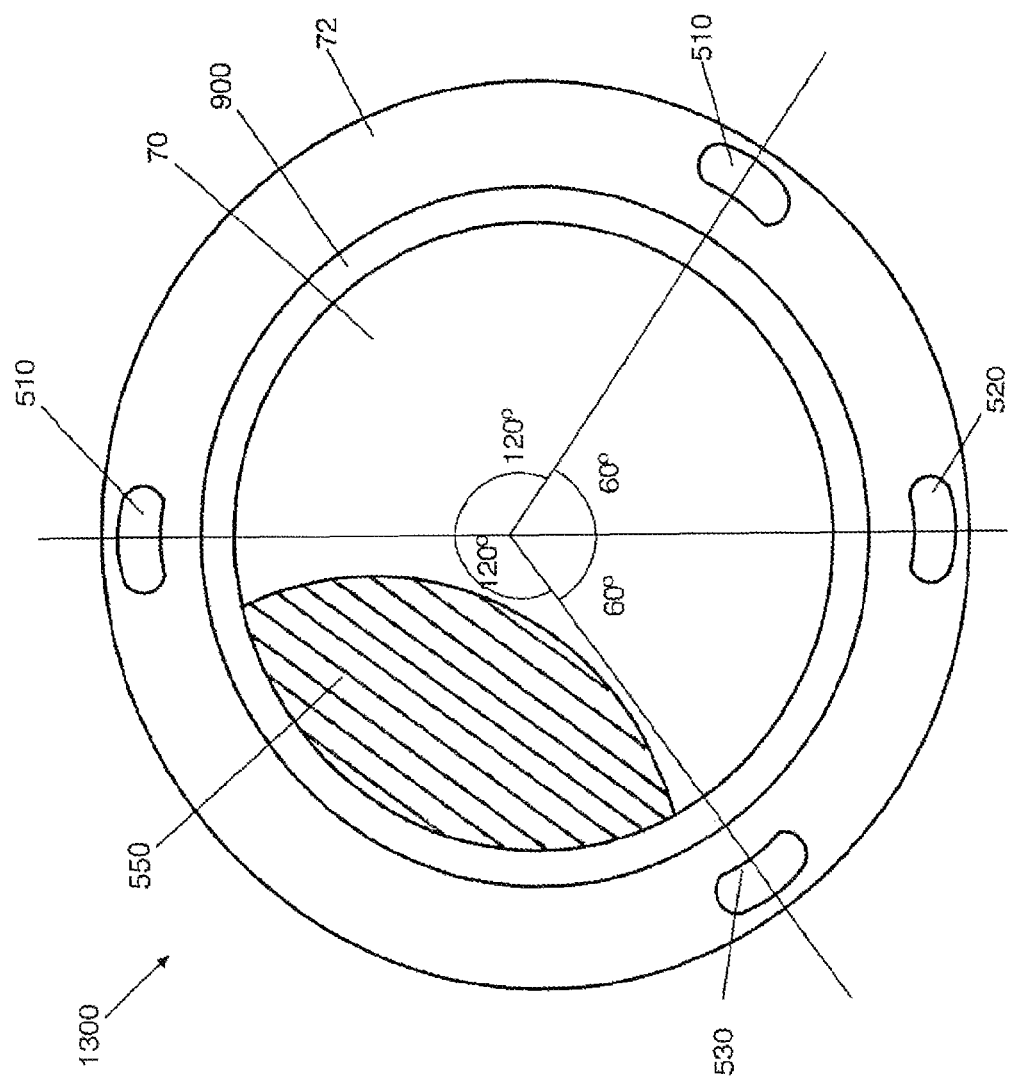
FIG. 16 is a top view of an intraocular implant according to a sixth example embodiment of the present invention.

In an alternative and sixth example embodiment, shown in FIG. 16, the lugs 510-540 are always located at predetermined positions with respect to the patient's eye and at least one lug is aligned with a measurable landmark of the eye rather than with the part of the lens having the different optical power. According to an example embodiment, the first lug is always located so that it is aligned at 0° (i.e. closest to the medial canthus or inner corner of the eye) with the principal meridian of anterior or posterior corneal curvature astigmatism measureable by optical coherence tomography (OCT) scanning during the lens surgery procedure. Alternatively, it is possible to align the lens with a landmark of the patient's body, such as the medial or lateral canthus itself. In this case, the optic 70 is formed relative to the lugs so that the part having the different optical power is formed at a rotational position relative to the first lug 510 so that the correct rotational registration is obtained when the implant 1300 is attached to the capsule with the first lug 510 aligned with the landmark in the patient's eye (such as a principal meridian or a canthus). In this manner, the surgeon can consistently form the incisions in the capsule to match the asymmetric pattern of the lugs 510-540 on the skirt 72, with an incision for the first lug 510 aligned with the landmark in all patients, irrespective of the asymmetry of the optic or the desired rotational registration, secure in the knowledge that the correct rotational registration will be obtained so long as the correct implant 1300 is fitted. Again, this arrangement is particularly suitable where the optic 70 is asymmetrical, for example for the treatment of astigmatism by a toric lens. Of course, the first lug need not be located at the principal meridian or the canthus in the patient's eye. Any predetermined position can be used so long as it is consistent for all patients.

The concept of consistently providing at least one lug 510 at a predetermined position with respect to a patient's eye on all lenses further reduces the likelihood of implantation with erroneous rotational registration, and allows the accuracy of rotational registration to be improved. Thus, the present invention provides a plurality of implants, at least one of which has optical or other asymmetry, in which at least one lug 510 is provided for all the implants at a predetermined location on the peripheral skirt 72 for engaging with a void or incision provided at the same rotational position in the capsule of the eye.

It should be noted that this concept of locating at least one lug at a fixed position with respect to the eye is separable from but can also be synergistically combined with the above-mentioned concept of providing the lugs 510-540 at asymmetrical positions.

Figure 17:
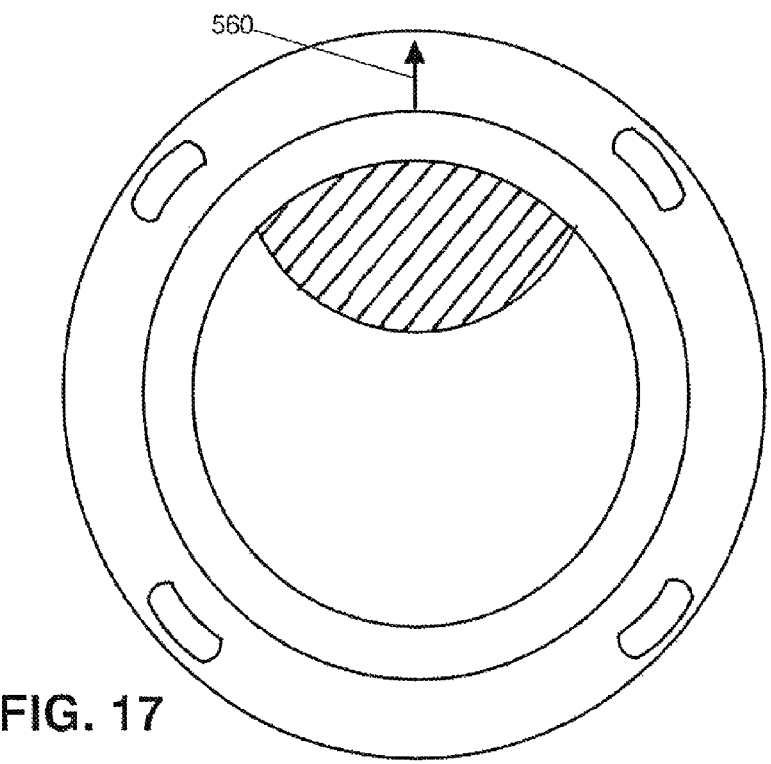
FIG. 17 is a top view of an intraocular implant according to a seventh example embodiment of the present invention.

In addition to, or instead of, any one or more of the three directly preceding concepts, it is possible to etch the peripheral skirt 72 with a marking to show the surgeon the required rotational registration. Seventh and eighth example embodiments using this concept are shown in FIGS. 16 and 17. In FIG. 16, an arrow 560 is provided to show the central location of the part of the optic having the different optical power 550. By contrast, in FIG. 17 an arrow 560 is provided to show the surgeon the correct rotational registration of the optic—for example, the surgeon is aware that the implant should be implanted with the arrow pointing along the relevant meridian or towards the relevant canthus.

Markings may be provided on the peripheral skirt 72 in any suitable manner. For example, the markings are etched using an excimer laser, which takes approximately 0.5 seconds. Providing markings on the peripheral skirt 72 is effective because at that position they are less likely to scatter or reflect incident light to affect the vision of the patient. However, it is preferable to keep the amount of marking to a minimum to avoid scattering and reflection effects and to reduce irritation to the capsule.

Figure 19:
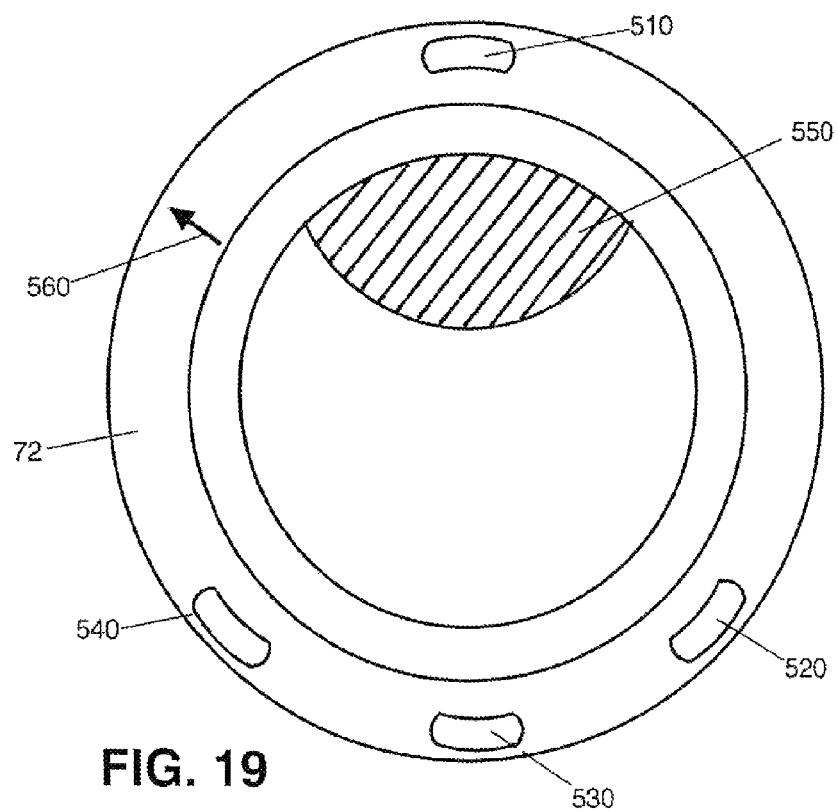
FIG. 19 is a top view of an intraocular implant according to a ninth example embodiment of the present invention.
Figure 20:
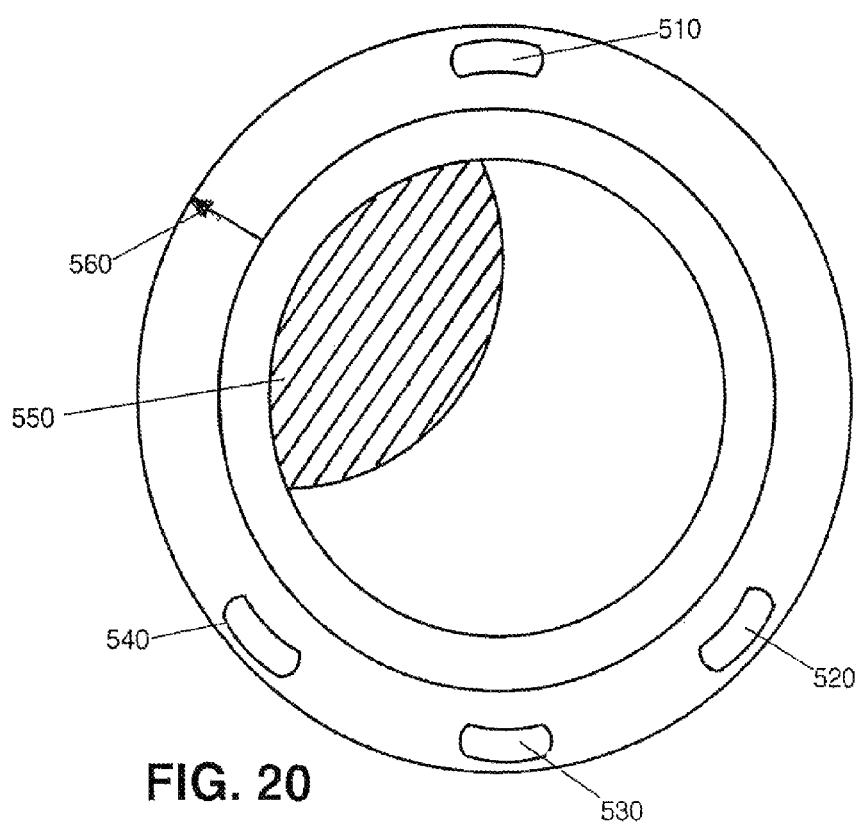
FIG. 20 is a top view of an intraocular implant according to a tenth example embodiment of the present invention.

In each case, the concept of providing markings on the skirt may be combined with asymmetrical positioning of the lugs. FIGS. 19 and 20 are the same as FIGS. 15 and 16, except that a marking 560 is further included on the skirt 72.

In the ninth example embodiment shown in FIG. 19 the first lug 510 is used to indicate the central location of the part of the optic 70 having the different optical power 550 and the arrow 560 indicates the correct rotational registration of the optic—for example, the surgeon is aware that the implant should be implanted with the arrow pointing along the relevant meridian or towards the relevant canthus.

In the tenth embodiment shown in FIG. 20 the arrow 560 is used to indicate the central location of the part of the optic 70 having the different optical power 550 and the first lug 510 indicates the correct rotational registration of the optic 70—for example, the surgeon is aware that the implant should be implanted with the first lug 510 at the relevant meridian or aligned with the relevant canthus.

The arrangements shown in FIGS. 15 and 17 have the advantage that only one arrangement of lugs 510-540 or only one marking need be used for all implants having a predetermined asymmetry. However, the responsibility then rests with the surgeon to ensure that the incisions in the capsule are made at the appropriate positions to ensure correct rotational registration. As explained above, the lens orientation can be referenced to measureable landmarks such as the principal meridian of anterior or posterior corneal curvature astigmatism measureable by OCT scanning during the lens surgery procedure. Therefore, in surgery the surgeon can determine the landmark and then provide the lugs with correct rotational offset from that landmark to achieve the desired rotational registration in the eye. Thus, in practice the arrangements shown in FIGS. 15 and 17 allow highly accurate rotational registration for individual patients.

Figure 18:
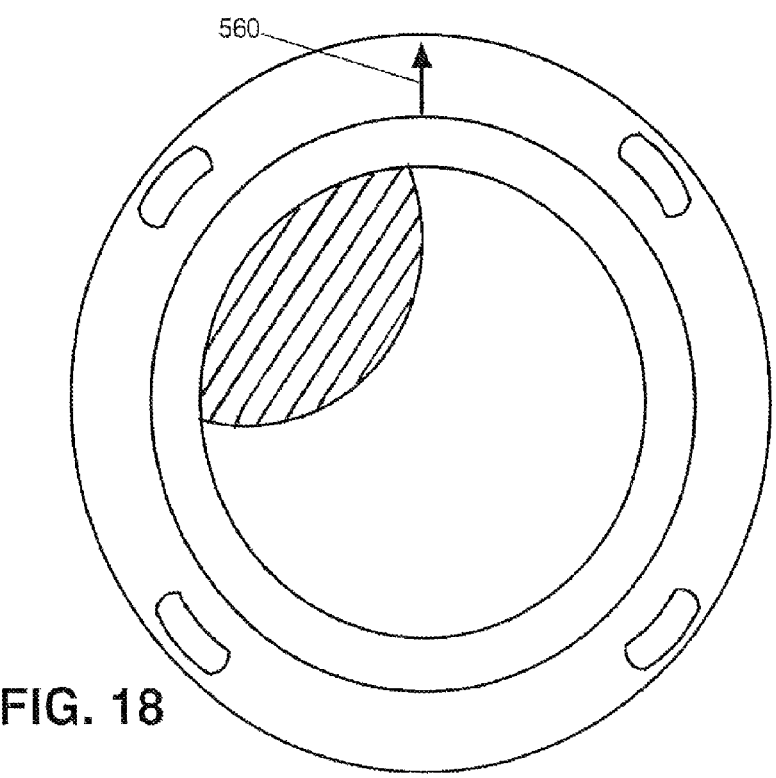
FIG. 18 is a top view of an intraocular implant according to an eighth example embodiment of the present invention.

By contrast, the arrangements shown in FIGS. 16 and 18 have the advantage that the surgeon can consistently form incisions in the capsule with the same rotational registration, irrespective of the patient and his specific condition, thus reducing the likelihood of incorrect rotational registration. For example, in surgery the surgeon can determine the relevant meridian using OCT and then make incisions/voids so that when the implant is fitted the desired lug is aligned with that meridian. The asymmetrical arrangement of the lugs ensures that the surgeon places the correct lugs in the correct incisions. In the event that OCT scanning is not available during surgery, using a canthus as the landmark allows reasonably accurate rotational registration of the optic in the eye. However, a plurality of implants needs to be made for each predetermined asymmetry, implants with optics having the same asymmetry among the plurality of implants having different positioning of lugs 510-540 or markings 560 to show varying rotational registration. Thus, there is a need to make a greater number of implants.

Although more complicated to produce, the arrangements shown in FIGS. 19 and 20 provide and additional layer of safety in ensuring correct rotational registration of the implant. Nonetheless, it may be preferable to provide asymmetrical lugs without markings, as in FIGS. 15 and 16, in order to reduce scattering and reflection effects and to reduce irritation to the capsule due to the markings.

The arrangement shown in FIG. 16 is preferred. According to an example embodiment, the width of the lugs 510-540 in the radial direction of the implant is substantially the same as the width of the peripheral skirt 72.

The present invention also provides a method of eye surgery, in which a patient first visits an eye surgeon, optician, optometrist, ophthalmologist or other professional who measures the shape of the cornea, using OCT, wavefront measurement or any other suitable means. Based on the measurement, an implant according to the present invention is made with an asymmetrical optic such as a toric lens such that when the implant is fitted in the patient's eye with the correct rotational registration the patient's vision is corrected. For example, the lugs of the implant are asymmetrically arranged, for example as described with reference to FIG. 16. Subsequently, a surgeon fits the implant by re-measuring the shape of the cornea, for example to determine the principal meridian of anterior or posterior corneal curvature astigmatism; carrying out a capsulotomy and forming voids at predetermined positions corresponding to the positions of the lugs, for example with at least one void aligned with the principal meridian of anterior or posterior corneal curvature astigmatism; and engages the lugs with the respective voids to mount the implant with correct rotational registration and at the correct position in the X, Y and Z directions.

In each of the third to tenth example embodiments shown in FIGS. 12-20, the lugs are provided on a peripheral skirt 72. However, the lugs may also be provided on haptics instead, the positions of the haptics being adjusted to the extent necessary to achieve the lug arrangements and the ensuing advantages.

When the implant of any of the foregoing embodiments is located adjacent to the inside of a capsulotomy made in the anterior part of the capsule (an "anterior capsulotomy")—this location is called the "bag fixated" location—the lugs will face toward the front of the eye. This situation applies to the first example embodiment, since it assumes the use of haptics, and also to the second and subsequent example embodiments. In addition the lugs can be placed on the posterior side of the device and be fixated in the bag using posterior facing lugs and voids in the posterior capsule. There may or may not be a posterior capsulotomy. In addition, where the implant of the second and subsequent embodiments is located adjacent to the outside of the anterior capsulotomy (the "sulcus fixated" location), the lugs will be facing toward the back of the eye. The reverse will apply where the implant is located adjacent the inside or outside of a posterior capsulotomy.

Realizations of the above-described first and second example embodiments are shown in FIGS. 21-28.

Figure 21:
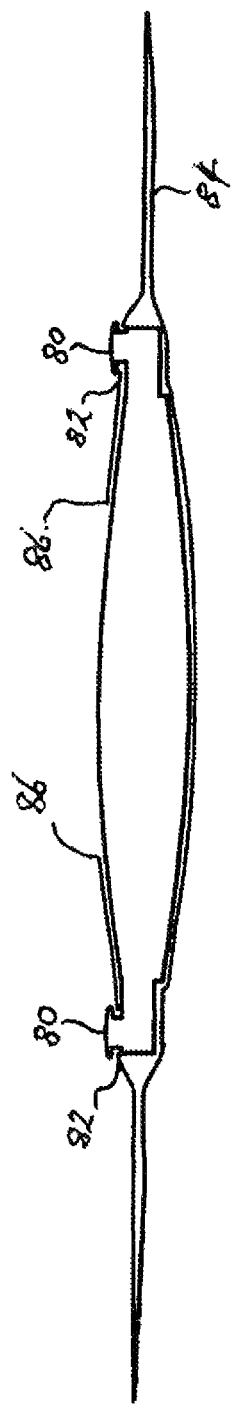
Figure 22:
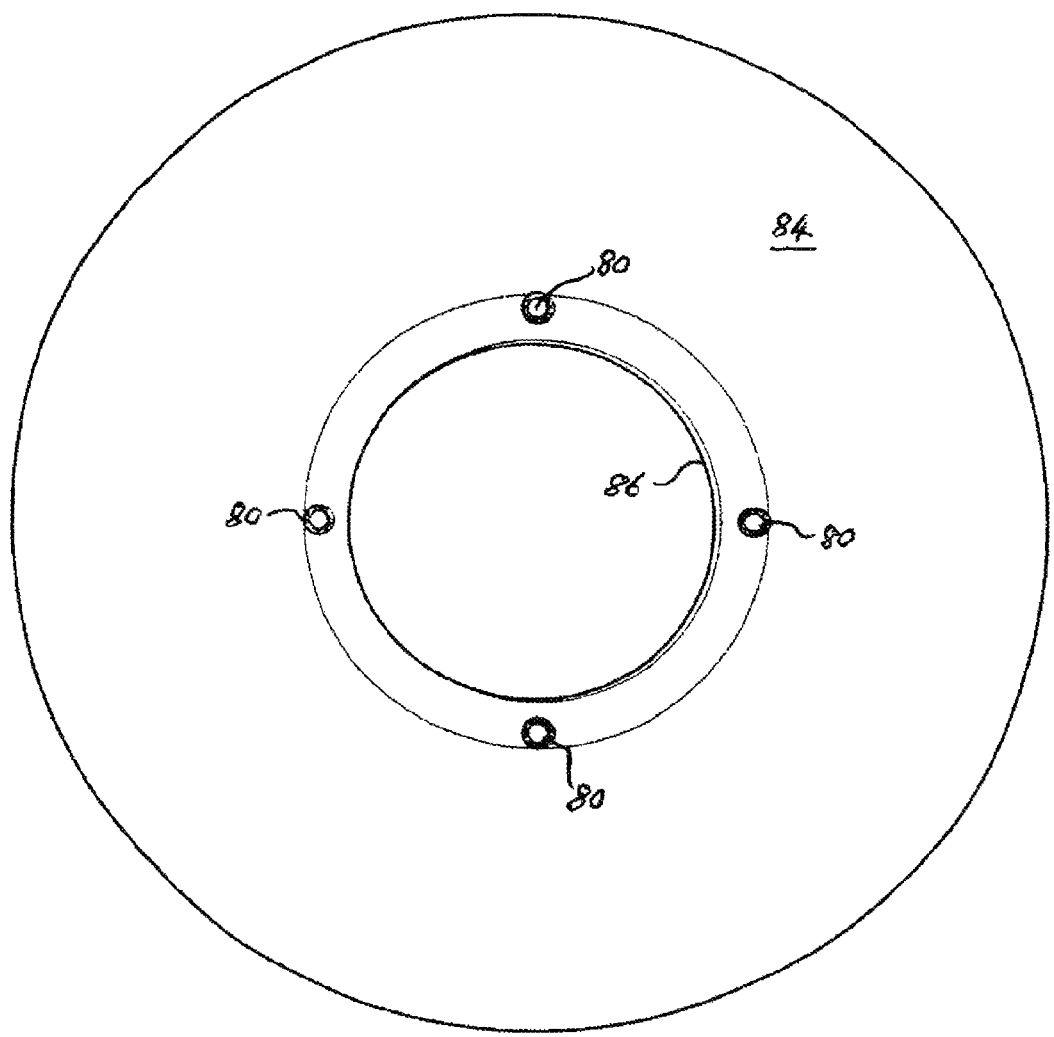

FIG. 21 shows a side view of a lens without haptics located within a capsular bag. The lugs 80 are anterior-facing, i.e. facing toward the front of the eye, and are engaged with holes 82 created in the anterior wall of the bag 84. An anterior capsulotomy 86 can also be seen. FIG. 22 shows a front view of this arrangement, though with a somewhat wider capsulotomy 86 than that shown in FIG. 21.

A similar configuration, but involving a lens with haptics, is shown in FIGS. 23 and 24. The lens itself is shown in FIG. 23, while the lens in the bag is shown in FIG. 24. This time the lugs 90 are situated further away from the center of the lens 92 and therefore engage with holes 94 located further away from the anterior capsulotomy 96.

Figure 25:
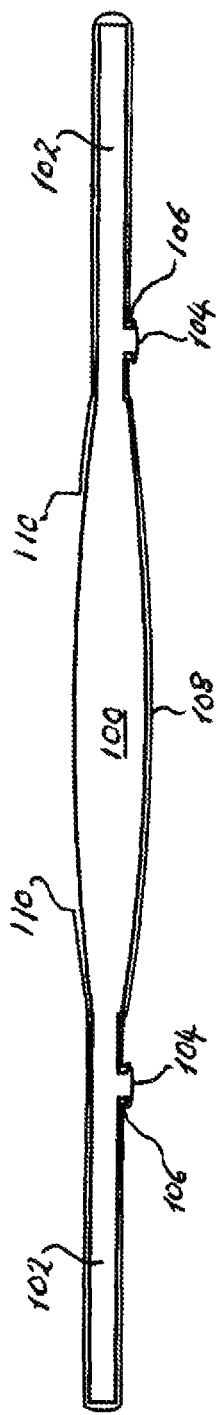

FIG. 25 depicts a side view of a lens 100 with haptics 102 and posterior-facing lugs 104, which engage with holes 106 made in the posterior wall 108 of the bag. Also shown is an anterior capsulotomy 110.

Figure 26:
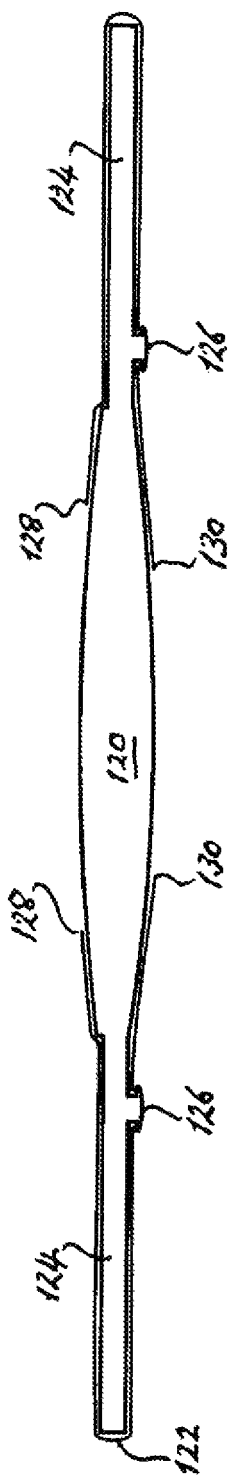

FIGS. 26 and 27 are top and front views, respectively, of a lens 120 located in the bag 122, in which the lens has haptics 124 and posterior-facing lugs 126 inserted into posterior capsular voids. This time a capsulotomy 128, 130 has been made in both the anterior and posterior walls of the bag. Incidentally, FIG. 27 shows, for clarity, a copy of FIG. 26, but with reduced dimensions to align with the diameter of the bag shown in FIG. 27.

Figure 28:
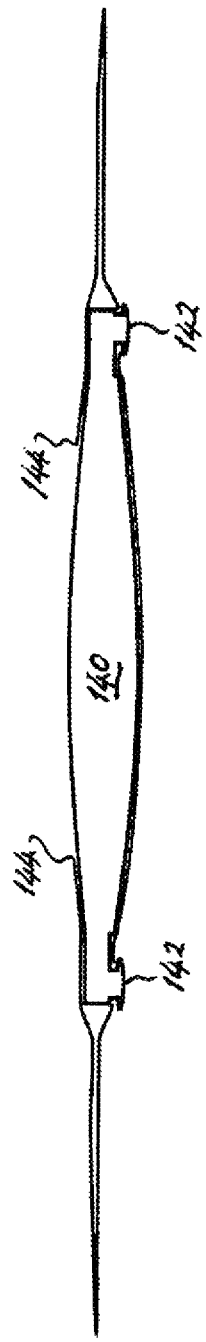

Finally, an example of a hapticless lens 140 having posterior-facing lugs 142 engaging posterior voids is shown in FIG. 28. The bag has an anterior capsulotomy 144.

It will be appreciated that the implants of the third to eighth embodiments shown in FIGS. 12-20 can be located with respect to the capsular bag as described in FIGS. 21-28.

The use of the lugs in the foregoing example embodiments has the following advantages:
  the implant can be reliably and repeatably placed at a desired position in the X-Y plane (coronal plane) vis-à-vis the capsule;
  the implant can be very securely attached to the capsule;
  the implant can be fixed at a desired rotational orientation, which is required where the lens has an asymmetrical optic (e.g. where there is variable optical power in the lens or where there is a toric optic);
  since the implant can be held firmly against the capsule by the lugs (via the mushroom head), the implant can be made to have a well defined placement in the Z-direction (see FIG. 8), which enables a reliable definition of the optical power of the implant to be obtained.

Instead of using only one lens as an implant, it may be necessary to employ a multi-lens design. Examples of such a design are illustrated and discussed in US 2003/0130732 mentioned earlier. The multiple lens would form a unit and be secured to the capsule via either anterior-facing or posterior-facing lugs. Alternatively, both anterior and posterior facing lugs may be provided on respective front and back lenses, these lugs engaging with voids made in the anterior and posterior walls of the bag.

In an eleventh example embodiment of the invention, the implant is not a lens, but a plug or bung. Such an implant is not required to have any refractive properties, but serves merely to close a fenestration or other aperture in the capsule. An example of this is shown in FIG. 29. Indeed, FIG. 29 shows two examples of different diameter, depending on the size of the fenestration to be closed. It can be seen that this implant is flat and therefore has no optical power. Other configurations having no optical power may also be used. Furthermore, the lugs in this situation are not required to accurately establish the rotational position of the implant (which would be the case with an asymmetrical lens), but merely to secure the plug to the capsule. The plug may or may not be opaque, depending on the location of the aperture being closed.

A specific example of a plug in use with a bag is not shown in the drawings. However, a typical scenario might be as shown in FIG. 12, in which the lens was replaced by a plug such as shown in FIG. 29. The lugs engage with holes in one wall of the bag and block off an opening or fenestration, which might be larger than or smaller than the capsulotomy shown as item 86 in FIG. 21.

Fenestrations that might be closed off using the plug are, for example, fenestrations introduced into the capsule in order to facilitate the entry of an instrument for evacuating the lens material. In this respect, femtosecond lasers are often used to cut the lens into very small cubes or slices, so that they can be evacuated through a small-bore instrument or cannula. The cannula can be introduced into the capsule through such a fenestration. In addition, the plug can be used to provide tectonic support, in order to keep compartments in the eye physically separate. It is also useful as a means of preventing silicone oil from moving forward into the anterior segment of the eye.

Although a total of two lugs are shown in the first embodiment and four in the other embodiments, there may be as many lugs as there are haptics in the first embodiment (there may also be fewer lugs than haptics), and fewer than, or more than, four lugs in the other embodiments. The main criterion for selecting the number of lugs is to ensure a secure fixing of the implant to the capsule.

Also, it should be appreciated that the haptics shown in the first example embodiment are representative only, and may take other shapes.

The lugs are shown as being unitary with the haptics (first embodiment) or the lens extension (other embodiments). However, in a twelfth example embodiment they are instead formed as separate items, which are later attached by suitable means to the haptics or extension.

Figure 30A:
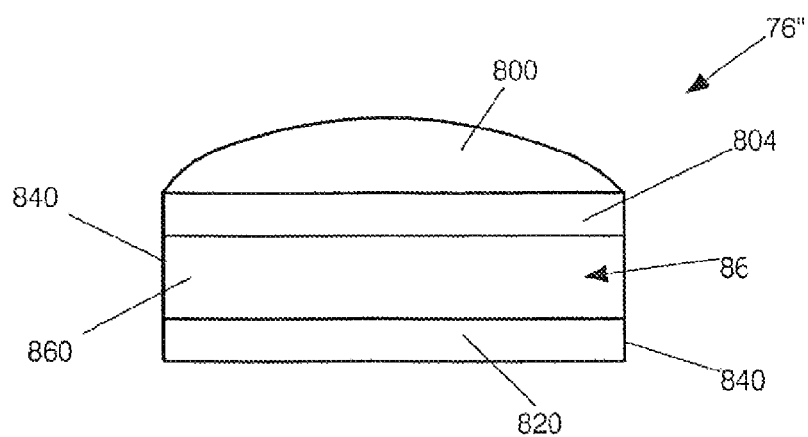
FIGS. 30A-C respectively are a front elevation, a cross-section through the line B-B shown in FIG. 30A, and a perspective view of a lug according to a twelfth example embodiment of the invention.
Figure 30B:
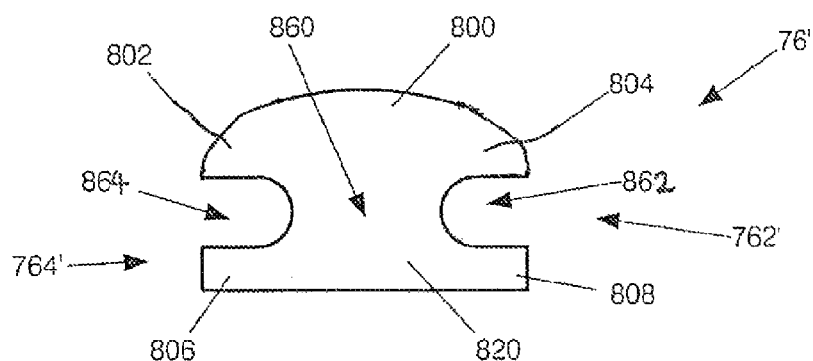
Figure 30C:
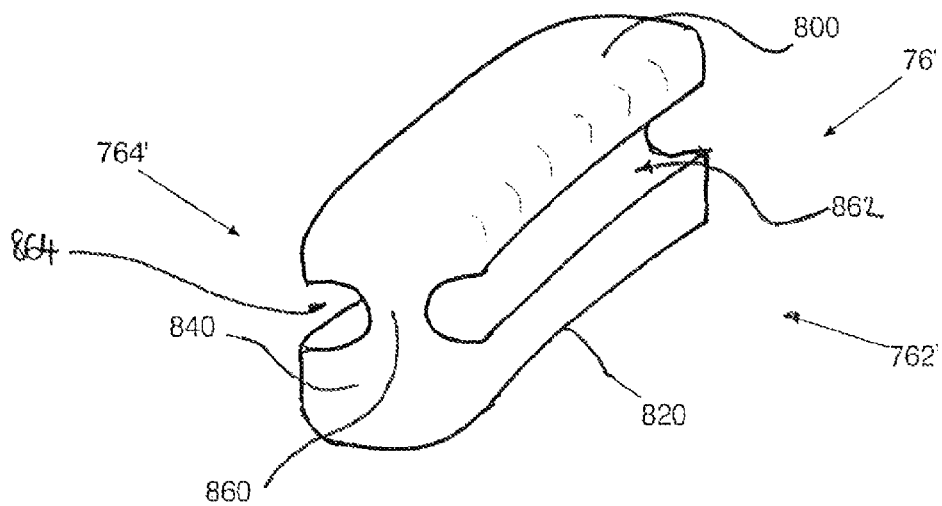

Thus, FIGS. 30A-C respectively show a front elevation, a side elevation and a perspective view of a separate lug 76". The separate lug 76" of the tenth example embodiment is substantially the same as the lug 76' shown in FIG. 14 but is formed separately from the peripheral skirt 72. Thus, it includes a top 800 and a bottom 820 joined by a stem 860. As shown in FIG. 14, in the implant 1100 the lugs 76' are what may be described as kidney-shaped. In particular, like the lugs 76' shown in FIG. 14, they include substantially two semicircles at the ends joined by radially inner and outer side edges 762', 764'. Again, the radially inner and outer edges 762', 764' are not straight but instead are curved. In more detail, the radially inner edge 762' is concave whereas the radially outer edge 764' is convex and parallel to the radially inner edge 762'. For example, the radially outer edge 764' is shaped so that it will follow the line of the circumference of the peripheral skirt 72 to which it is intended to be attached and the radially inner edge 762' is shaped so that it will follow the line of the inner edge of the peripheral skirt 72 to which it is intended to be attached.

Between the top 800 and the bottom 820 there are formed a radially inner groove 862 and a radially outer groove 864 running along the length of the radially inner and outer sides 762', 764' respectively. The inner and outer grooves 862, 864 sandwich the stem 860 between them. The grooves 862, 864 are distinct from one another so that the top 800 is provided with respective inner and outer lips 802, 804. The height of the grooves in the Z direction is, for example, substantially the same as or slightly greater than the thickness of the capsule wall. Thus, the height of the grooves is, for example, 30 to 50 μm. The depth of the grooves in the X-Y plane extending away from the inner and outer edges 762, 762 respectively is, for example, also in the range 30 to 50 μm.

The top 800 of the lug 76" may have a curved upper surface—that is, the upper surface of the top 800 curves upwards out of the X-Y plane. This assists the surgeon in placing the lugs 76" in the voids (incisions) created in the capsule and minimises irritation to the iris.

The bottom 820 of the lug 76" is, for example, flat. If the skirt 72 onto which the lug is to be attached is also flat, the lug 76" can be easily attached with a known orientation in the X-Y plane. Moreover, because grooves 862, 864 are formed in the sides of the lug 76", the bottom is provided with lips 806, 808 flaring outwards away from the stem 860. This increases the surface area of the bottom 820 of the lug 76" compared, for example, to the lugs shown in FIG. 9. The increased surface area of the bottom helps to ensure that the lug 76" can be securely attached to the skirt 72. Moreover, because the grooves 862, 864 are distinct from one another and the stem 860 extends along the whole length of the lug 76", the surface area of the bottom 820 is further increased, thereby further improving the security with which the lug 76" can be attached to the skirt.

The overall height of the lugs 76 in the Z direction and the degree of curvature is also chosen to provide a low profile to avoid chafing the iris. The overall geometry of the lugs is likewise selected to avoid causing irritation to the patient.

The provision of an elongated lug 76" of this shape has all the advantages discussed above.

Similarly, the provision of a kidney-shape is advantageous for the reasons discussed above. Moreover, providing the outer edge 764' with the same curvature as the edge of the skirt 72 on which the lug 76" is to be mounted has the advantage that the lug can be located on the skirt 72 in the radial direction with the desired orientation by butting both the edge of the skirt 72 and the outer edge 764' of the lug 76" against the same surface.

Figure 32:
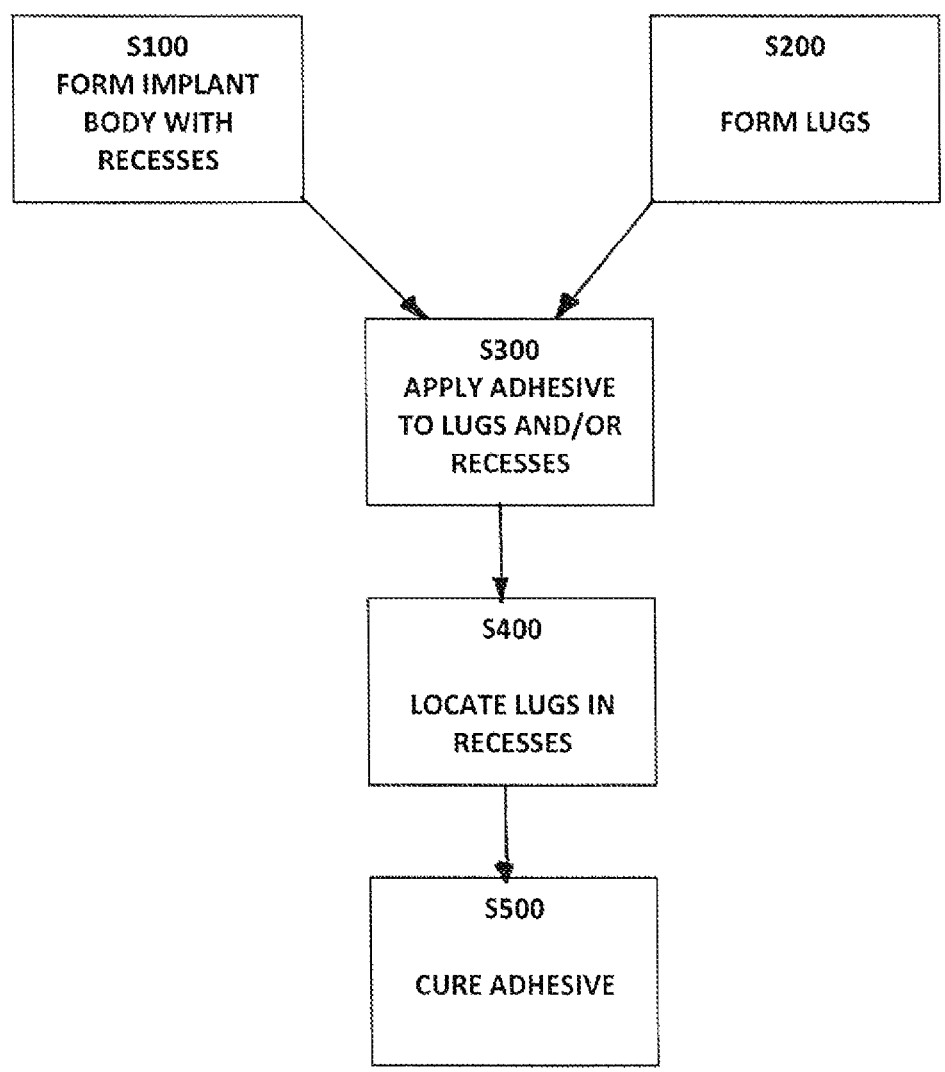
FIG. 32 is a flow chart showing a method of manufacturing the implant of the twelfth example embodiment of the present invention.

An example method of forming an implant will now be described with reference to FIG. 32. In a first step S100 an implant body, which does not have lugs, is formed. The implant body is made of any suitable biocompatible material such as silicone, but for example an acrylic and for further example hydroxy methyl methacrylate acrylic. The implant body can be formed by any suitable means, including moulding. According to an example embodiment, however, a block of implant body material is mounted to a steel base, for example using an adhesive or encasing the body in wax and mounting the wax body to the base. The base is then mounted to a lathe and the block of material is then turned, for example, using a diamond cutting tool. The turning process (spinning the block and moving a cutting tool towards and away from block, and moving the cutting tool in the X-Y plane) can be used to shape an implant body comprising the optic 70, the groove 900 and the peripheral skirt 72. The rotational speed of the block may be relatively small compared to the speed of movement of the cutting tool to provide asymmetrical features. Features of the implant body can also be formed by moving a cutting tool, such as a drill, towards and away from block whilst moving the cutting tool in the X-Y plane but without spinning the block.

Those skilled in the art will appreciate that turning and other shaping procedures can be used to provide optics 70 with a variety of desired geometries, taking account of the refractive index of the implant body material, the desired power of the optic and the desired rotational asymmetry (for example to create a toric lens).

Figure 31:
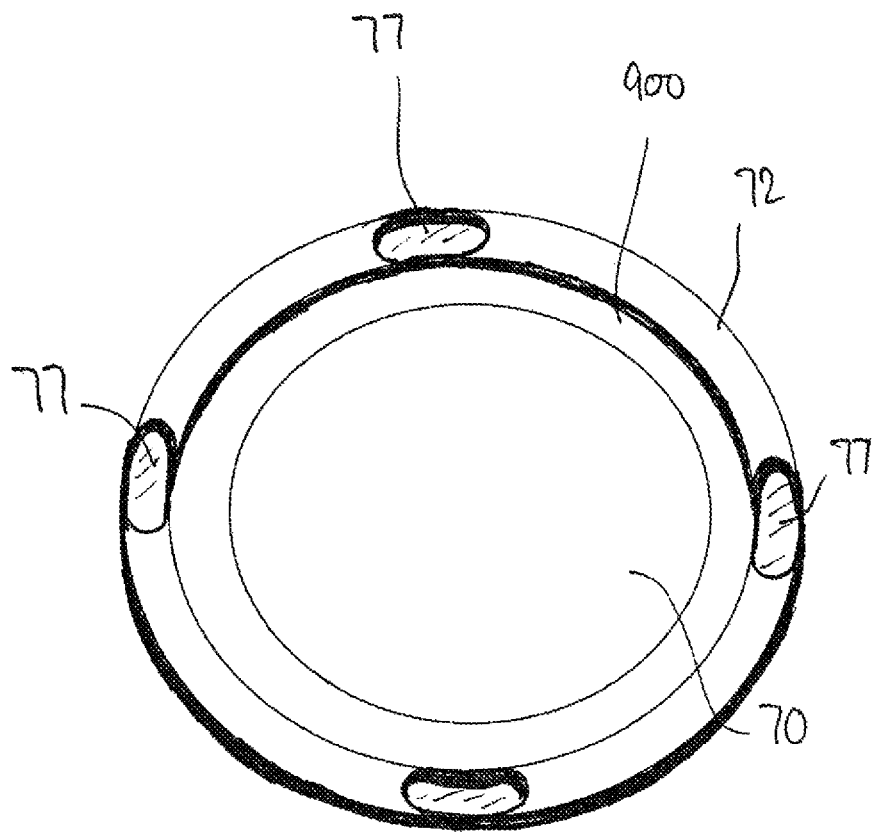
FIG. 31 is a perspective view of an implant body according to the twelfth example embodiment of the present invention.

In addition, the peripheral skirt of the implant body is preferably, but need not be, provided with recesses 77 for the lugs 76" (see FIG. 31). The recesses 77 have substantially the same footprint as the lugs 76" that are to be mounted in them and the depth of the recesses 77 is selected so that when the lugs 76" are mounted in them, the lugs 76' protrude a desired distance above the surface of the peripheral skirt 72. The recesses 77 can be formed by any desired method including turning or excimer laser. For example, the recesses are formed using a diamond tipped drill or other machine tool.

Lugs 76", for example as shown in FIG. 30, are made independently in a second step S200. They can, but need not, be made of the same material and using a similar procedure—turning a block of material, moulding or otherwise shaping. Other materials include silicone and other acrylics. Step S200 can be carried out at the same time as, before or after step S100.

In step S300, adhesive is applied to at least one of the bottom surface of the recesses 77 and the bottom surface of the lugs 76". The lugs 76" are then mounted in the recesses 77 in step S400. Since the recesses 77 have substantially the same footprint as the lugs 76", they fit into the recesses 77 with a tight tolerance fit. The adhesive is then cured in step S500. The adhesive may be a UV curable adhesive, in which case the implant can be bathed in UV light to cure the adhesive and secure the lugs 76" in the implant body.

The lugs 76" can be attached to the peripheral skirt 72 (or to haptics) by any suitable technique. For example, if the tolerance fit between the recesses 77 and the lugs 76" is sufficiently tight, the adhesive may be omitted. An alternative example method is to attach the lugs 76" by laser welding. A carbon dioxide or diode infrared laser can be used to create heat to weld the lugs in place. Where laser welding is used, it is possible but by no means necessary to omit the recesses 77.

Alternative modes of attachment are also possible, including providing the lug 76" with a pin on the bottom surface which can be pressed into the skirt 72 if it is made of suitable soft material or can be press-fitted into a hole provided in the skirt 72 for the purpose. The skirt 72 may be provided with the pins as well or instead. In addition, fluidic self-assembly techniques may be used.

The provision of lugs that are separate from the skirt is advantageous for a number of reasons. First, it allows the lens optic to move or flex for accommodating lens designs. For flexible extensions a common material is silicone. The lugs may be constructed from silicone or acrylic material, as is common with current intraocular lens implants.

In addition, by forming the optic 70 (and skirt 72) separately from the lugs, and then mounting the lugs 76" to the skirt 72, it is possible to form only a single implant body or optic for any predetermined asymmetry. Thus, each optic can be mass-manufactured and the lugs can also be mass-manufactured, thereby significantly reducing the cost of manufacture. The mass-manufactured lugs 76" can then be mounted to the mass-manufactured optics 70. Rotational registration for one or more individuals can then be achieved by mounting the lugs 76" on the skirt 72 in predetermined positions in the manner illustrated in FIGS. 15 and 16. Of course, it will be appreciated that the lugs 76" can be mounted either symmetrically or asymmetrically around the skirt 72. Providing the skirt 72 with recesses 77 improves the accuracy of sitting of the lugs. However, it is not essential to provide the recesses and this may increase the flexibility with which lugs may be subsequently sited on any particular skirt. In other words, by not providing the recesses, it is possible to manufacture a large number of implant bodies with an optic having a particular asymmetry and then set the rotational registration only later by mounting the lugs at desired positions.

Accordingly, in addition to an implant comprising a plurality of lugs, the present invention also provides an implant body without lugs, lugs separate from the implant body and a method of manufacturing an implant comprising a plurality of lugs by mounting the lugs to the implant body without lugs.

Figure 33:
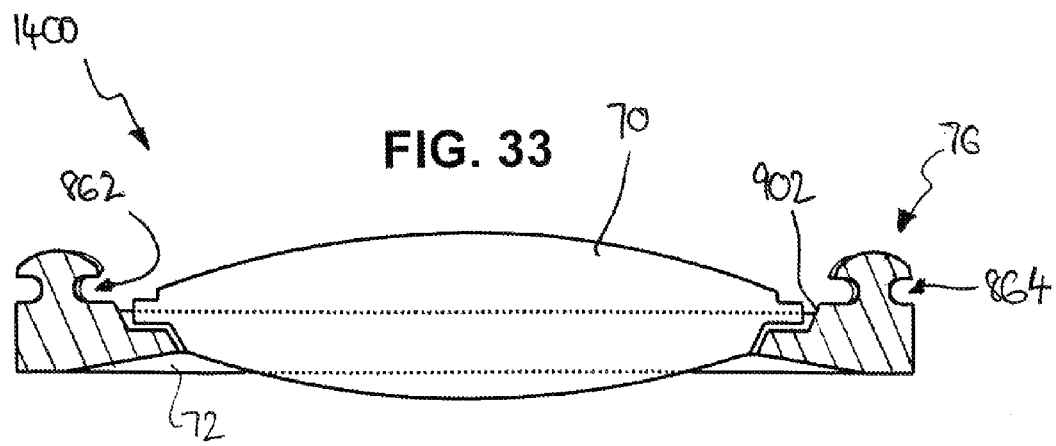
FIG. 33 is a cross-section view of an intraocular implant according to a thirteenth example embodiment of the present invention.
Figure 34:
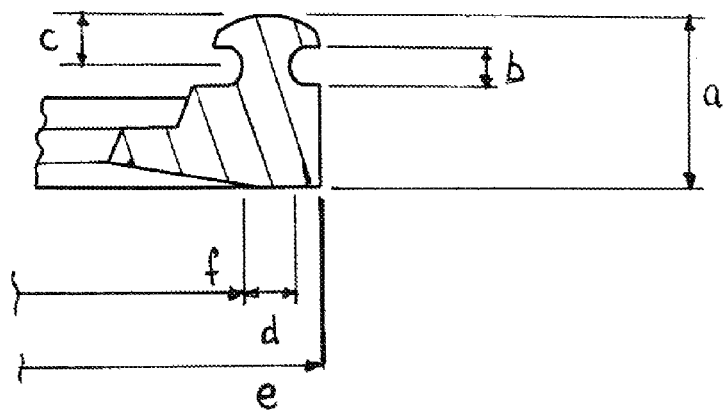
FIG. 34 is a sectional view of the lug and a skirt according to the thirteenth example embodiment.
Figure 35:
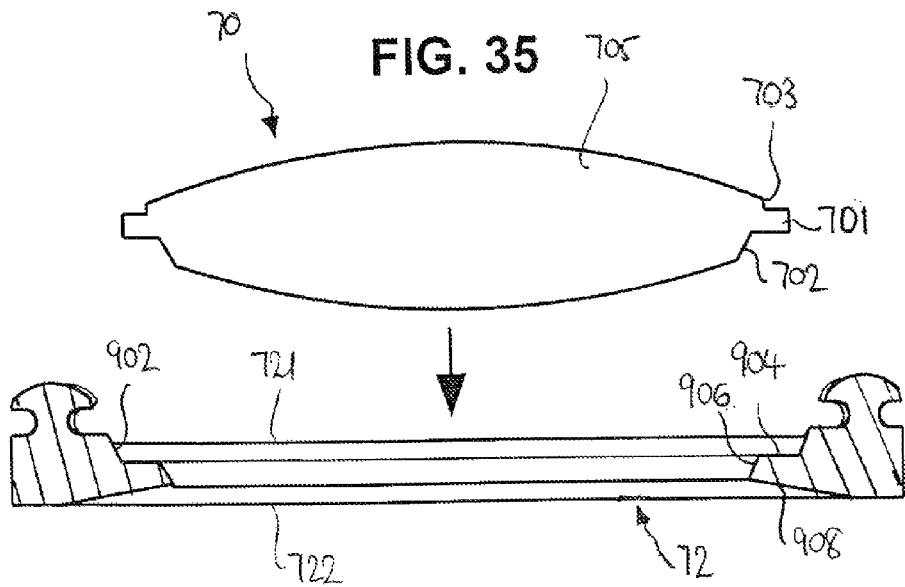
FIG. 35 is an exploded view of the implant according to the thirteenth example embodiment.

An implant 1400 according to a thirteenth, example embodiment of the present invention is shown in FIGS. 33 to 35. In this embodiment, the implant 1400 comprises a separately formed optic 70 and skirt 72. The skirt 72 is a ring-shaped body having an upper surface 721 and a bottom surface 722 and is provided with lugs 76. For example, there are four equidistantly-spaced lugs 76 although only two are shown for ease of illustration. As previously, the lugs 76 have inner and outer grooves 862 and 864 respectively, with the bottom surface of the grooves 862, 864 being slightly raised above the upper surface 721 of the skirt 72. For example the lugs 76 are kidney-shaped.

In addition, the skirt 72 is provided with a circumferential groove, which in this case is not closed on the radially inner side. The groove is formed of a radially outer side wall 902, which in this case slants radially inwardly travelling in a direction from the upper surface 721 to the groove bottom surface 904. Radially inwards of the groove bottom surface 904 there is provided an inner edge surface 906, which also slants radially inwardly travelling in a direction from the groove bottom surface 904 towards the skirt bottom surface 722. Finally, a joining surface 908 slants radially outwardly and downwardly to join the bottom of the inner edge surface 906 and the skirt bottom surface 722 (see FIG. 35). At least the groove bottom surface 904 and the inner edge surface 906 form a mounting portion.

Viewing FIG. 34, the height 'a' of the skirt 72 from the skirt bottom surface 722 to the top of the lug 76 is, according to one example, between 0.4 mm and 0.6 mm, according to another example, between 0.42 mm and 0.52 mm, and according to another example, substantially 0.47 mm. The width 'b' of each of the grooves 862, 864 is according to one example between 0.05 mm and 0.15 mm, according to another example, between 0.07 mm and 0.13 mm, and, according to another example, substantially 0.10 mm. The distance 'c' from the top of each lug 76 to the middle of each of the grooves 862, 864 is for example between 0.08 mm and 0.18 mm, for example between 0.10 mm and 0.16 mm, and according to another example substantially 0.13 mm. The width 'd' of the stem 860 in the radial direction of the skirt 72 is for example between 0.09 mm and 0.19 mm, in another example, between 0.11 mm and 0.17 mm, and in a further example, substantially 0.14 mm. The radius 'e' of the skirt 72 is for example, between 2.7 mm and 3.7 mm, in another example between 3.0 mm and 3.4 mm, and in a further example substantially 3.2 mm. The radius 'f' of the bottom of the inner groove 862—that is, the distance from the center of the skirt 72 to the bottom of the inner groove 862—is for example between 2.45 mm and 3.45 mm, in another example between 2.86 mm and 3.06 mm, and in a further example substantially 2.96 mm. The maximum length of the elongated lug 76 (measured tangentially to the circumferential direction of the skirt) is for example, between 0.7 mm and 0.9 mm, in another example between 0.77 mm and 0.87 mm, and in a further example substantially 0.82 mm. The same or similar dimensions or ranges of dimensions can also be used in any of the foregoing embodiments.

The separate optic 70 comprises a radial extension 701 extending around the periphery of the main body 705 of the optic 70. The radial extension 701 has substantially parallel upper and lower surfaces. The lower surface of the extension 701 joins a slanting lower side surface 702 of the optic main body 705 and the upper surface of the extension 701 joins an upper side surface 703 of the optic main body 705. The upper side surface 703 is substantially orthogonal to the upper surface of the radial extension 701. The diameter of the optic 70 as measured across the optic main body 705 to the upper side surface 702 is for example, between 4.2 mm and 6.2 mm, in another example, between 4.7 mm and 5.7 mm, and in a further example substantially 5.2 mm.

The implant 1400 can be assembled by moving the optic 70 and skirt 72 relative to one another, as shown in FIG. 35, so that the bottom surface of the radial extension 701 of the optic 70 abuts or lies over the groove bottom surface 904, as shown in FIG. 33. The lower side surface 702 of the optic main body 705 and the inner edge surface 906 of the skirt 72 both slant at substantially the same angle and consequently the inner edge surface 906 guides the lower side surface 702 and hence the optic 70 into the correct position with respect to the skirt 72 during mounting and then supports it in position. The optic 70 can be held in place by the skirt 72 by means of a press fit or by applying an adhesive to any one or more of the bottom of radial extension 701, lower side surface 702, groove bottom surface 904 and inner edge surface 906 prior to mounting. If an adhesive is used, it is for example UV curable to allow rapid curing.

As intended to be shown in FIG. 33, the upper surface of the extension 701 is substantially level with the bottom of the inner groove 864, with a gap between them. As previously described, the capsule wall forming the edge of the capsulotomy may drop over the side wall 902 along its circumference to provide a barrier. Alternatively, the capsulotomy may be sized so that its edge abuts the upper side surface 703 to form a barrier, or at least spans the groove between the skirt 72 and the upper surface of the radial extension 701 of the optic 72.

Figure 36:
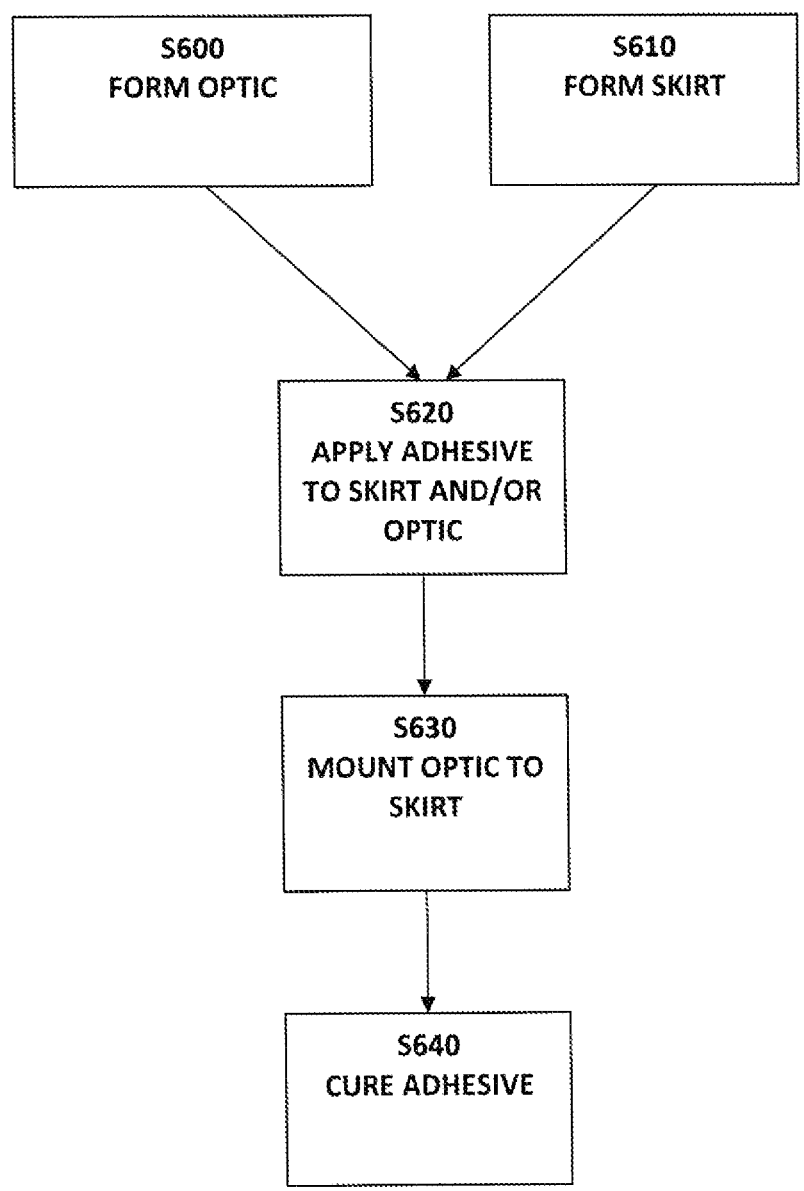
FIG. 36 is a flow chart depicting a method of manufacturing the implant of the thirteenth example embodiment of the present invention.

An example method of forming an implant 1400 will now be described with reference to FIG. 36. In a first step S600 an optic 70 is formed. The optic 70 is made of any suitable biocompatible material, such as silicone for example an acrylic and in another example hydroxy methyl methacrylate acrylic. The optic 70 can be formed by any suitable means, including moulding and turning. Those skilled in the art will appreciate that other shaping procedures can be used to provide optic 70 with a variety of desired geometries, taking account of the refractive index of the implant body material, the desired power of the optic and the desired rotational asymmetry (for example to create a toric lens).

The skirt 72 is made independently in a second step S610 and can, but need not, be made of the same biocompatible material and using similar procedures—turning a block of material, moulding or otherwise shaping. Step S610 can be carried out at the same time as, before or after step S600.

In step S620, adhesive is applied to any one or more of the bottom of radial extension 701, lower side surface 702, groove bottom surface 904 and inner edge surface 906 prior to mounting. The optic 70 is then mounted to the skirt in step S630. The optic 70 may fit into the skirt 72 with a tight tolerance fit. The adhesive is then cured in step S640. The adhesive may be a UV curable adhesive, in which case the implant can be bathed in UV light to cure the adhesive and secure the optic 70 in the skirt 72 to form the implant body 1400.

In the present embodiment, the lugs 76 are formed integrally with the skirt 72. However, they may be formed separately and attached to the skirt 72 before or after the optic 70 is mounted to the skirt 72. Again, the lugs 76 can be attached to the peripheral skirt 72 as explained with reference to FIGS. 30 to 32 or by any other suitable means.

Other ways of attaching the optic 70 to the skirt 72 are contemplated. For example, if the radially outer side wall 902 is formed substantially orthogonal to the groove bottom surface 904 and a sufficiently tight tolerance fit is provided between the radially outer side wall 902 and the radial extension 701 of the optic 70, the adhesive may be omitted. An alternative method is to attach the optic 70 by laser welding. A carbon dioxide or diode infrared laser can be used to create heat to weld the optic 70 in place.

Alternative modes of attachment are also possible, including providing the groove bottom surface 902 with a pin which can be pressed into the radial extension 701 if it is made of suitable soft material or can be press-fitted into a hole provided in the radial extension 701, or vice versa, i.e. the pin can be provided on the optic 70, or both.

The formation of the optic 70 and the skirt 72 separate from one another has a number of significant advantages. In particular, the skirts 72 can be cheaply produced on a comparatively large scale irrespective of the optics 70 they are to be used with. Similarly, different optics 70 can be easily and cheaply produced on a large scale for use with the same skirt 72. Moreover, if an optic 70 is provided with rotational geometry, as discussed above (for example, toric lenses), then optics of any particular geometry can be produced on a large scale and subsequently fitted in skirts with the correct rotational alignment with respect to the lugs 76.

It should be appreciated that the expression "skirt" has been used in the foregoing for convenience. This should be understood to mean any suitable frame or other means for carrying lugs to engage with the capsule and for holding/mounting the optic, whereby the optic can be held by the capsule.

Accordingly, the present invention also provides a skirt or frame for an implant body (with or without lugs), an optic separate from but mountable to the skirt, and a method of manufacturing an implant by mounting the optic to the skirt.

It should also be appreciated that an integral implant body having the geometry shown in FIG. 34 can be provided, in which the skirt and the optic are not separate.

Figure 37:
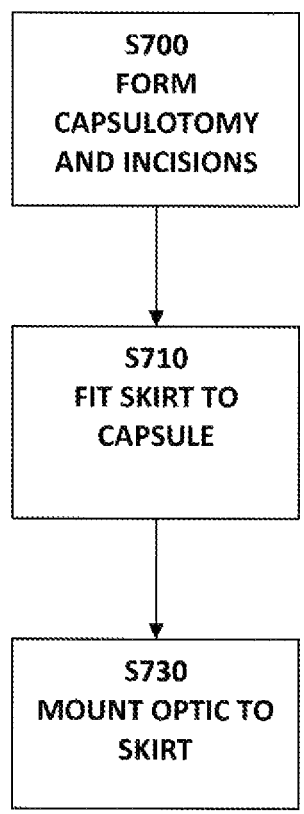
FIG. 37 is a flow chart depicting a method of implanting an implant lens according to an example embodiment of the invention.

Referring to FIG. 37, according to another embodiment, the invention includes a method of ophthalmic surgery including, in step S700 forming a capsulotomy and incisions in the lens capsule. In step S710 the method includes fitting a skirt to the capsule, for example by inserting lugs 74 or the other lugs described herein into incisions in the capsule. The method further includes, in S730, mounting the optic 70 to skirt 72.

While the implant, apart from the haptics, has been shown in the drawings as being essentially circular in shape, it may take any shape corresponding to the capsule opening against which it is to be located. Thus, where the implant is or includes a lens, it may be oval or elliptical in shape, for example, instead of circular.

Although the use of the implant of the present invention has generally been described in connection with cataract surgery, alternative uses are envisaged. Thus, the implant can be also be employed in surgical procedures for treating myopia, hyperopia, astigmatism or presbyopia (refractive lens exchange surgery).

Although the peripheral portion or skirt 72 has consistently been shown as a continuous band surrounding the optic 70, it should be understood that the expressions peripheral portion and skirt are not limited to such an arrangement and also include arrangements in which the peripheral portion or skirt does not form a continuous band but is instead broken up into a number of different portions, each extending radially outwards from the optic 70.

In addition, the expression "asymmetry" and corresponding expressions should not be interpreted in the strict literal sense but are intended to include arrangements in which the optic 70 or other portion is symmetrical but includes varying geometry radially and/or more particularly circumferentially, such as one lug has a different shape to another lug, or has the same shape but is positioned so that the shape is position in a circumferentially different manner. As an example, one lug 76 in FIG. 12A could be positioned with its longitudinal axis being aligned along a radius of the implant rather than perpendicular to it. Similarly, these expressions include arrangements in which the optic 70 or the lugs are asymmetrical about a line in the X-Y plane passing through the center of the optic and the center of at least one lug, irrespective of rotation of the lens in the X-Y plane.

Likewise, the expression "lug" and corresponding expressions are intended as and are to be interpreted as generic expressions denoting any protrusion which can engage with a void or incision in the capsule.

In addition, the expression "optic" is intended to have a broad meaning unless the context requires otherwise and includes within its compass, for example, blanks, plugs and bungs.

Moreover, the expression "mount" and corresponding expressions are intended broadly. For example, where an optic is described as being mounted to a skirt this encompasses mounting the skirt to the optic. This applies mutatis mutandis to other situations.

Where the terms "upper", "lower" and like terms are used, they are used for descriptive purposes only and are intended to provide a frame of reference only for the item being described. Thus, although lugs may be described as being provided on an upper surface, the corresponding implant can be fitted with the lugs either anterior or posterior facing.

The foregoing description has been given by way of example only and it will be appreciated by a person skilled in the art that modifications can be made without departing from the scope of the present invention.

The invention claimed is:

1. An intraocular implant for placement in an eye, the implant comprising:
a main portion and a peripheral portion peripheral to the main portion,
wherein the peripheral portion is a skirt surrounding and peripheral to the main portion,
the implant having at least two lugs extending from the peripheral portion in a direction out of a plane of the implant,
the lugs each having a head and a neck, the neck having a length of 30 to 50 μm and at least one lug being elongated in a circumferential direction relative to the implant,
at least one of the lugs having a radially inner groove and a separate radially outer groove whereby the radially inner groove and the separate radially outer groove facilitate the lugs being received to fit snugly in openings in the lens capsule to hold the implant securely in place,
the skirt presenting a circumferential groove formed on a same surface of the skirt as the lugs, the circumferential groove being disposed between the optic and the lugs,
the lugs being for engagement with corresponding voids provided in a capsule of the eye, and
wherein the lugs are positioned in fixed locations with respect to the main portion, and
the lugs being asymmetrically arranged,
wherein a single orientation of the implant is determined by asymmetrical location of the lugs.

2. The intraocular implant according to claim 1, wherein the lugs are asymmetrically arranged by being located at positions asymmetric about at least one direction in the plane of the implant.

3. The intraocular implant according to claim 2, wherein a first distance between a first said lug and a second said lug, which is adjacent to the first said lug, is different than a second distance between the first said lug and a third said lug, which is adjacent to the first said lug on an opposite side to the second said lug.

4. The intraocular implant according to claim 3, wherein:
there are four lugs;
the first lug is located 120° from the fourth lug, which is adjacent to the first lug;
the first lug is located 60° from the second lug, which is adjacent to the first lug on the opposite side to the fourth lug;
the third lug is located 120° from the fourth lug, which is adjacent to the third lug; and
the third lug is located 60° from the second lug, which is adjacent to the third lug on an opposite side to the fourth lug.

5. The implant according to claim 1, wherein the main portion comprises a lens having multiple optical powers.

6. The implant according to claim 5, wherein the main portion comprises a toric lens.

7. An intraocular implant for placement in the eye, the implant comprising:
a main portion and a peripheral portion peripheral to the main portion,
wherein the peripheral portion is a skirt surrounding and peripheral to the main portion, the main portion being asymmetrical,
the implant having at least two lugs extending from the peripheral portion in a direction out of a plane of the implant,
the lugs each having a head and a neck, the neck having a length of 30 to 50 μm and at least one lug being elongated in a circumferential direction relative to the implant,
at least one of the lugs having a radially inner groove and a separate radially outer groove whereby the radially inner groove and the separate radially outer groove facilitate the lugs being received to fit snugly in openings in the lens capsule to hold the implant securely in place, the skirt presenting a circumferential groove formed on a same surface of the skirt as the lugs, the circumferential groove being disposed between the optic and the lugs, wherein the lugs are positioned in fixed locations with respect to the main portion, the lugs being for engagement with corresponding voids provided in a capsule of the eye, wherein the lugs are asymmetrically arranged and positioned in a fixed location with respect to the main portion, the lugs being located with respect to the main portion such that, when the voids are provided in the capsule at a predetermined landmark, the implant can be implanted by engaging the voids to achieve correct rotational registration of the main portion with respect to the eye and wherein a single orientation of the implant is determined by the asymmetrical location of the lugs.

8. The implant according to claim 7, wherein the main portion comprises a tonic lens.

9. The implant according to claim 7, wherein the main portion comprises a lens having multiple optical powers.

* * * * *